(12) United States Patent
Matsui et al.

(10) Patent No.: US 7,252,929 B2
(45) Date of Patent: Aug. 7, 2007

(54) METHODS FOR IDENTIFYING ALPHA PDGFR AGONISTS AND ANTAGONISTS

(75) Inventors: Toshimitsu Matsui, Kobe (JP); Stuart A. Aaronson, New York, NY (US); Jacalyn H. Pierce, Pukalani, HI (US)

(73) Assignee: United States of America, as represented by the Secretary, Dept of Health & Human Services, Washington, DC (US)

( * ) Notice: Subject to any disclaimer, the term of this patent is extended or adjusted under 35 U.S.C. 154(b) by 169 days.

(21) Appl. No.: 10/700,249

(22) Filed: Nov. 3, 2003

(65) Prior Publication Data

US 2005/0112582 A1  May 26, 2005

Related U.S. Application Data

(60) Continuation of application No. 09/769,987, filed on Jan. 25, 2001, now Pat. No. 6,660,488, which is a division of application No. 08/460,656, filed on Jun. 2, 1995, now Pat. No. 6,228,600, which is a division of application No. 08/439,095, filed on May 11, 1995, which is a continuation of application No. 07/915,884, filed on Jul. 20, 1992, now abandoned, which is a continuation of application No. 07/308,282, filed on Feb. 9, 1989, now abandoned.

(51) Int. Cl.
*C12Q 1/00* (2006.01)

(52) U.S. Cl. ............................ 435/4; 435/7.1; 435/7.2; 436/514; 436/547; 436/548

(58) Field of Classification Search .................... 435/4, 435/7.2, 7.1; 436/514, 547, 548
See application file for complete search history.

(56) References Cited

U.S. PATENT DOCUMENTS

| | | | |
|---|---|---|---|
| 4,487,829 A | 12/1984 | Sharp et al. | |
| 4,699,880 A | 10/1987 | Goldstein | 435/172.2 |
| 4,766,073 A | 8/1988 | Murray et al. | |
| 5,094,941 A | 3/1992 | Hart | 435/7.9 |
| 5,100,774 A | 3/1992 | Rakowicz-Szulczynska | 435/6 |
| 5,219,727 A | 6/1993 | Wang et al. | 435/6 |
| 5,268,358 A | 12/1993 | Fretto | 514/12 |
| 5,371,206 A | 12/1994 | Kelly et al. | |
| 5,468,468 A | 11/1995 | LaRochelle et al. | 424/1.49 |
| 5,833,986 A | 11/1998 | LaRochelle et al. | 424/143.1 |
| 5,863,739 A | 1/1999 | LaRochelle et al. | 435/7.2 |
| 5,965,359 A | 10/1999 | Matsui et al. | 435/6 |
| 6,043,211 A | 3/2000 | Williams et al. | |
| 6,110,737 A | 8/2000 | Escobedo et al. | |

FOREIGN PATENT DOCUMENTS

| | | |
|---|---|---|
| WO | WO 90/10013 | 9/1990 |
| WO | WO 93/10805 | 6/1993 |
| WO | WO 93/11223 | 6/1993 |
| WO | WO 94/19016 | 9/1994 |
| WO | WO 96/20718 | 7/1996 |

OTHER PUBLICATIONS

Wells Biochemistry 1990, vol. 29(37): 8509-8517.*
Chapter 14: Computational Complexity Protein Structure Prediction, and the Levinthal Paradox pp. 492-495 in The Protein Folding Problem and Tertiary Structure Prediction, Merz editor. 1994 Birkhauser publisher Boston.*
Brenner et al. Trends in Genetics 1999 vol. 15(4): 132-133;).*
Bork et al. Trend in Genetics 2000, vol. 14, p. 398.*
Claesson-Walsh et al. Identification and Structural Analysis of the A Type Receptor for Platelet-derived Growth Factor, *J. Biol. Chem.*, 264: 1742-1747 (1989).
Nister et al. "Expression of Messenger RNAs for Platelet-derived Growth Factor and Transforming Growth Factor-$\alpha$ and Their Receptors in Human Malignant Glioma Cell Lines," *Can. Res.*, 48: 3910-3918 (1988).
Ronnstrand et al. Characterization of Two Monoclonal Antibodies Reactive with the External Domain of the Platelet-derived Growth Factor Receptor, *J. Biol. Chem.*, vol. 283 (1988).
Escobedo et al. A Common PDGF Receptor Is Activated by Homodimeric A and B Forms of PDGF, *Science*, vol. 240 (1988).
Claesson-Welsh et al. cDNA Cloning and Expression of a Human Platelet-Derived Growth Factor (PDGF) Receptor Specific for B-Chain-Containing PDGF Molecules, *Molecular and Cellular Biology*, vol. 8, No. 8 (1988).
Johnson et al. Platelet-Derived Growth Factor: Identification of Constituent Polypeptide Chains, *Biochemical and Biophysical Research Communications*, vol. 104, No. 1 (1982).
Heldin et al. Binding of different dimeric forms of PDGF to human fibroblasts: evidence for two separate receptor types, *EMBO Journal*, vol. 7, No. 5, (1988).
Gronwald et al. Cloning and expression of a cDNA coding for the human platelet-derived growth factor receptor: Evidence for more than one receptor class, *Proc. Nat'l. Acad. Sci.*, vol. 85 (1988).
Hart et al. Synthesis, Phosphorylation, and Degradation of Multiple Forms of the Platelet-derived Growth Factor Receptor Studied Using a Monoclonal Antibody, *Journal of Biol. Chem.*, vol. 262, No. 22, (1987).

(Continued)

*Primary Examiner*—Long V. Le
*Assistant Examiner*—Jacob Cheu
(74) *Attorney, Agent, or Firm*—Needle & Rosenberg, PC

(57) ABSTRACT

Discoveries are disclosed that show particular aspects of recombinant DNA technology can be used successfully to produce a hitherto unknown type of human Platelet-Derived Growth Factor (PDGF) receptor protein free of other PDGF receptors. These proteins can be produced from DNA segments in cells in various functional forms. These forms variously enable biochemical and functional studies of these novel receptors as well as production of antibodies. Means are described for determining the level of expression of genes for specific types of PDGF receptor proteins, for example, by measuring mRNA in cells with PDGF receptor type-specific DNA probes or by measuring antigen in biological samples with type-specific antibodies.

7 Claims, 27 Drawing Sheets

OTHER PUBLICATIONS

Betsholtz et al., "Coexpression of a PDGF-Like Growth Factor and PDGF Receptors in a Human Osteosscoma Cell Line: Implications for Autocrine Activation" *Cell*, 39: 447-457 (1984).

Matsui et al., "Isolation of A Novel Receptor cDNA Establishes the Existence of Two PDGF Receptor Genes" *Science*, 243: 800-804, (1989).

Mikl et al., "An Efficient Directional Cloning System to Construct cDNA Libraries Containing Full-Length Inserts at High Frequency" *Gene*, 83(1) : 137-146 (1989).

Glese et al., The Role of Individual Cysteine Residues in the Structure and Function of the *v-exis* Gene Product, *Science*, 236: 1315-1318 (1987).

Claesson-Welsh et al., cDNA Cloning and Expression of a Human Platelet-Derived Growth Factor (PDGF) Receptor Specific for *B*-type Chain PDGF Molecules, a *Mol. Cell, Biol*, 8(8): 3476-3486 (1988).

Hart et al., "Two Classes of PDGF Receptor Recognize Different Isoforms of PDGF" *Science*, 240: 1529-1531 (1988).

Anderson et al. "Binding of SH2 Domains of Phospholipase $C_\gamma$, GAP, and Src to Activated Growth Factor Receptors" *Science* 250:979-982 (Nov. 16, 1990).

Research News "Oncogenes Evoke New Cancer Therapies" *Science* 249:1376-1378 (Sep. 21, 1990).

Moran et al. "Src homology region 2 domains direct protein-protein interactions in signal transduction" *Proc. Natl. Acad. Sci. USA* 87:8622-8626 (Nov. 1990).

Kypta et al. "Association between the PDGF Receptor and Members of the src Family of Tyrosine Kinases" *Cell* 62:481-492 (Aug. 10, 1990).

Heidaran et al. "Chimeric $\alpha$-and $\beta$-Platelet-derived Growth Factor (PDGF) Receptors Define Three Immunoglobulin-like Domains of the $\alpha$-PDGF Receptor That Determine PDGF-AA Binding Specificity" *J. Biol. Chem.* 265:18741-18744 (Nov. 5, 1990).

Felder et al. "Kinase Activity Controls the Sorting of the Epidermal Growth Factor Receptor within the Multivesicular Body" *Cell* 61:623-634 (May 18, 1990).

Morrison et al. "Platelet-Derived Growth Factor (PDGF)-Dependent Association of Phospholipase C-$\gamma$ with the PDGF Receptor Signalling Complex" *Mol. Cell. Biol.* 10(5):2359-2366 (May 1990).

Ullrich et al. "Signal Transduction by Receptors with Tyrosine Kinase Activity" *Cell* 61:203-212 (Apr. 20, 1990).

Kaplan et al. "PDGF $\beta$-Receptor Stimulates Tyrosine Phosphorylation of GAP and Association of GAP with a Signaling Complex" *Cell* 61:125-133 (Apr. 6, 1990).

Reid et al. "Two forms of the basic fibroblast growth factor receptor-like mRNA are expressed in the developing mouse brain" *Proc. Natl. Acad. Sci. USA* 87:1596-1600 (Feb. 1990).

Williams "Signal Transduction by the Platelet-Derived Growth Factor Receptor" *Science* 243:1564-1570 (Mar. 24, 1989).

Williams "Signal Transduction by the Platelet-Derived Growth Factor Receptor Involves Association of the Receptor with Cytoplasmic Molecules" *Clin. Research* 37:564-568 (1989).

Fantl et al. "Mutations of the Platelet-Derived Growth Factor Receptor That Cause a Loss of Ligand-Induced Conformational Change, Subtle Changes in Kinase Activity, and Impaired Ability To Stimulate DNA Synthesis" *Mol. Cell. Biol.* 9(10):4473-4478 (Oct. 1989).

Morrison et al. "Direct Activation of the Serine/Threonine Kinase Activity of Raf-1 through Tyrosine Phosphorylation by the PDGF $\beta$-Receptor" *Cell* 58:649-657 (Aug. 25, 1989).

Bishayee et al. "Ligand-induced Dimerization of the Platelet-derived Growth Factor Receptor" *J. Biol. Chem.* 264(20):11699-11705 (Jul. 15, 1989).

van Driel et al. "Stoichiometric Binding of Low Density Lipoprotein (LDL) and Monoclonal Antibodies to LDL Receptors in a Solid Phase Assay" *J. Biol. Chem.* 264(16):9533-9538 (Jun. 5, 1989).

Heldin et al. "Dimerization of B-type Platelet-derived Growth Factor Receptors Occurs after Ligand Binding and Is Closely Associated with Receptor Kinase Activation" *J. Biol. Chem.* 264(15):8905-8912 (May 25, 1989).

Bell et al. "Effect of Platelet Factors on Migration of Cultured Bovine Aortic Endothelial and Smooth Muscle Cells" *Circulation Research* 65(4):1057-1065 (Oct. 1989).

Coughlin et al. "Role of Phosphatidylinositol Kinase in PDGF Receptor Signal Transduction" *Science* 243:1191-1194 (Mar. 3, 1989).

Keating et al. "Platelet-derived Growth Factor Receptor Inducibility Is Acquired Immediately after Translation and Does Not Require Glycosylation" *J. Biol. Chem.* 264(16):9129-9132 (Jun. 5, 1989).

Yarden et al. "Growth Factor Receptor Tyrosine Kinases" *Ann. Rev. Biochem.* 57:443-478 (1988).

Qiu et al. "Primary structure of c-*kit*: relationship with the CSF-1/ PDGF receptor kinase family—oncogenic activation of v-*kit* nvolves deletion of extracellular domain and C terminus" *EMBO Journal* 7(4):1003-1011 (1988).

Kazlauskas et al. "Different effects of homo0 and heterodimers of platelet-derived growth factor A and B chains on human and mouse fibroblasts" *EMBO Journal* 7(12):3727-3735 (1988).

Williams et al. "The Immunoglobulin Superfamily—Domains for Cell Surface Recognition" *Ann. Rev. Immunol.* 6:381-405 (1988).

Kornbluth et al. "Novel Tyrosine Kinase Identified by Phosphotyrosine Antibody Screening of cDNA Libraries" *Mol. Cell. Biol.* B(12):5541-5544 (Dec. 1988).

Escobedo et al. "Role of Tyrosine Kinase and Membrane-Spanning Domains in Signal Transduction by the Platelet-Derived Growth Factor Receptor" *Mol. Cell. Biol.* 8(12):5126-5131 (Dec. 1988).

Orchansky et al. "Phosphatidylinositol Linkage of a Truncated Form of the Platelet-derived Growth Factor Receptor" *J. Biol. Chem.* 263(29):15159-15165 (Oct. 15, 1988).

Escobedo et al. "A PDGF receptor domain essential for mitogenesis but not for many other responses to PDGF" *Nature* 335:85-87 (Sep. 1, 1988).

Ruta et al. "A novel protein tyrosine kinase gene whose expression is modulated during endothelia cell differentiation" *Oncogene* 3:9-15 (1988).

Nister et al. "A Glioma-Derived PDGF A Chain Homodimer Has Different Functional Activities from a PDGF AB Heterodimer Purified from Human Platelets" *Cell.* 52:791-799 (Mar. 25, 1988).

Keating et al. "Autocrine Stimulation of Intracellular PDGF Receptors in v-*SiS*-Transformed Cells" *Science* 239:914-916 (Feb. 19, 1988).

Williams et al. "The Stimulation of Paracrine and Autocrine Mitogenic Pathways by the Platelet-Derived Growth Factor Receptor" *J. Cell. Physiol. Supp.* 5:27-30 (1987).

Daniel et al. "Biosynthetic and Glycosylation Studies of Cell Surface Platelet-derived Growth Factor Receptors" *J. Biol. Chem.* 262(20):9778-9784 (Jul. 15, 1987).

Keating et al. "Processing of the Platelet-derived Growth Factor Receptor" *J. Biol. Chem.* 262(16):7932-7937 (Jun. 5, 1987).

Williams "Stimulation of Paracrine and Autocrine Pathways of Cell Proliferation by Platelet-Derived Growth Factor" *Clin. Res.* 36:5-10 (1987).

Peralta et al. "Primary Structure and Biochemical Properties of an $M_2$ Muscarinic Receptor" *Science* 236:600-605 (May 1, 1987).

Ronnstrand et al. "Purification of the Receptor for Platelet-derived Growth Factor from Procine Uterus" *J. Biol. Chem.* 262(7):2929-2932 (Mar. 5, 1987).

Roussel et al. "Tranforming potential of the *c-fms* proto-oncogene (CSF-1 receptor)" *Nature* 325:549-552 (Feb. 5, 1987).

Williams et al. "PDGF Receptors: Structural and Functional Studies" in *Advances in Gene Technology: Molecular Biology of the Endocrine System* (Puett et al., eds.), *ICSU Short Reports* 4:168-171 (1986).

Daniel et al. "Purification of the platelet-derived growth factor receptor by using an anti-phosphotyrosine antibody" *Proc. Natl. Acad. Sci. USA* 82:2684-2687 (May 1985).

Kimball et al. "Epidermal Growth Factor (EGF) Binding to Membranes Immobilized in Microtiter Wells and Estimation of EGF-Related Transforming Growth Factor Activity" *Biochemica et Biophysica Acta* 771:82-88 (1984).

van der Schall et al. "An Enzyme-Linked Lectin Binding Assay for Quantitative Determination of Lectin Receptors" *Anal. Biochem.* 140:48-55 (1984).

Williams et al. "Platelet-derived Growth Factor Receptors Form a High Affinity State in Membrane Preparations" *J. Biol. Chem.* 259(8):5287-5294 (Apr. 25, 1984).

Haynes et al. "Constitutive, long-term production of human interferons by hamster cells containing multiple copies of a cloned interferon gene" *Nucleic Acids Research* 11(3):687-706 (1983).

Williams et al. "Platelet-derived growth factor binds specifically to receptors on vascular smooth muscle cells and the binding becomes nondissociable" *Proc. Natl. Acad. Sci. USA* 79:5867-5870 (Oct. 1982).

Glenn et al. "Platelet-derived Growth Factor" *J. Biol. Chem.* 257(9):5172-5176 (May 10, 1982).

Heldin et al. "Interaction of Platelet-derived Growth Factor with Its Fibroblast Receptor" *J. Bio. Chem.* 257(8):4216-4221 (Apr. 25, 1982).

Ascoli et al. "Platelet-Derived Growth Factor Receptor Immunoreactivity in Mesothelioma and Nonneoplastic Mesothelial Cells in Serous Effusions" *Acta Cytologica, The Journal of Clinical Cytology and Cytopathology* 39(4):613-622 (Jul.-Aug. 1995).

Koyama et al. "Different Functions of the Platelet-Derived Growth Factor-α and -β Receptors for the Migration and Proliferation of Cultured Baboon Smooth Muscle Cells" *Circulation Research* 75(4):682-691 (Oct. 1994).

Tiesman et al. "Identification of a Soluble Receptor for Platelet-derived Growth Factor in Cell-conditioned Medium and Human Plasma" *Journal of Biological Chemistry* 268(13):9621-9628 (May 1993).

Eccleston et al. "Expression of Platelet-Derived Growth Factor (PDGF) and PDGF α- and β-Receptors in the Peripheral Nervous System: An Analysis of Sciatic Nerve and Dorsal Root Ganglis" *Developmental Biology* 155(2):459-470 (Feb. 1993).

LaRochelle et al. "Inhibition of Platelet-derived Growth Factor Autocrine Growth Stimulation by a Monoclonal Antibody to the Human α Platelet-derived Growth Factor Receptor" *Cell Growth & Differentiation* 4:547-553 (Jul. 1993).

Huston et al. "Single-chain immunotechnology of Fv analogues and fusion proteins" in: *Immunotechnology* (Eds. Gosling and Reen, published Portland Press, London) pp. 47-60 (1993).

Chaudry et al. "Expression of Platelet-derived Growth Factor and Its Receptors in Neuroendocrine Tumors of the Digestive System" *Cancer Res.* 52:1006-1012 (1992).

Allam et al. "Differential migratory response of U-2 OS osteosarcoma cell to the various forms of platelet-derived growth factor" *Biochimie* 74:183-186 (1992).

DeFeudis "PDGF Antibody and Restenosis" *Drug News & Perspectives* 5(1):49-51 (Feb. 1992).

Ferns et al. "Inhibition of Neointimal Smooth Muscle Accumulation After Angioplasty by an Antibody to PDGF" *Science* 253: 1129-1132 (Sep. 6, 1991).

Krane et al. "Increased Dermal Expression of Platelet-Derived Growth Factor Receptors in Growth-Activated Skin Wounds and Psoriasis" *The Journal of Investigation Dermatology* 96(6): 983-986 (Jun. 1991).

Yu et al. "Structural Coincidence of αPDGFR Epitopes Binding to Platelet-Derived Growth Factor-AA and a Potent Neutralicing Monoclonal Antibody" *J. Biol. Chem.* 269(14):10668-10674 (Apr. 8, 1994).

Yu et al. "Tyrosine Mutations within the α Platelet-Derived Growth Factor Receptor Kinase Insert Domain Abrogate Receptor-Associated Phosphatidylinositol-3 Kinase Activity without Affecting Mitogenic or Chemotactic Signal Transduction" *Mol. And Cell. Biol.* 11(7): 3780-3785 (Jul. 1991).

Heidaran et al. "Role of αβ Receptor Heterodimer Formation in β Platelet-derived Growth Factor (PDGF) Receptor Activation by PDGF-AB" *J. Biol. Chem.* 266(30): 20232-20237 (1991).

Kelly et al. "Platelet-derived Growth Factor (PDGF) Stimulates PDGF Receptor Subunit Dimerization and Intersubunit *trans*-Phosphorylation" *J. Biol. Chem.* 266(14): 8987-8992 (1991).

Vassbotn et al. "A monoclonal antibody against PDGF B-chain inhibits PDGF-induced DNA synthesis in C3H fibroblasts and prevents binding of PDGF to its receptor" *Biochem. Biophys. Acta* 1054: 246-249 (1990).

Majesky et al. "PDGF Ligand and Receptor Gene Expression during Repair of Arterial Injury" *J. Cell Biol.* 111:2149-2158 (1990).

Hird et al. "Immunotherapy with Monoclonal Antibodies" *Genes and Cancer In: Immunotherapy and Monoclonal Antibodies* (published by J. P. Wiley & Sons Ltd.) pp. 183-189 (1990).

Queen et al. "A humanized antibody that binds to the interleukin 2 receptor" *Proc. Natl. Acad. Sci. USA* 86:10029-10033 (Dec. 1989).

Ashmun et al., "Monoclonal Antibodies to the Human CSF-1 Receptor (c-fms Proto-Oncogene Product) Detect Epitopes on Normal Mononuclear Phagocytes and on Human Myeloid Leukemic Blast Cells" *Blood* 73(3): 827-837 (Feb. 1989).

LaRochelle et al. "Immunochemical Localization of the Epitope for a Monoclonal Antibody that Neutralizes Human Platelet-Derived Growth Factor Mitogenic Activity" *Mol. Cell. Biol.* 9(8):3538-3542 (Aug. 1989).

Seifert et al. "Two Different Subunits Associate to Create Isoform-specific Platelet-derived Growth Factor Receptors" *J. Biol. Chem.* 264(15):8771-8778 (May 25, 1989).

Fleming et al. "Autocrine mechanism for v-*sis* tranformation requires cell surface localization of internally activated growth factor receptors" *Proc. Natl. Acad. Sci. USA* 86:8063-8067 (Oct. 1989).

Williams et al. "Signal Transduction by the Platelet-Derived Growth Factor Receptor" *Cold Spring Harbor Symposium on Quant. Biol.* pp. 455-465 (1988).

Hart et al. "Biochemical Evidence for Multiple Classes of Platelet-Derived Growth Factor Receptor" In: *Growth Factors and Their Receptors: Genetic Control and Rational Application* (published by Alan R. Liss, Inc.) pp. 297-305 (1989).

Hart et al. "Two Classes of PDGF Receptor Recognize Different Isoforms of PDGF" *Science* 240:1529-1531 (Jun. 10, 1988).

Escobedo et al. "Platelet-derived Growth Factor Receptors Expressed by cDNA Transfection Couple to a Diverse Group of Cellular Responses Associated with Cell Proliferation" *J. Biol. Chem.* 263(3):1482-1487 (1988).

Keating et al. "Ligand activation causes a phosphorylation-dependent change in platelet-derived growth factor receptor conformation" *J. Biol. Chem.* 263: 12805-12808 (Sep. 15, 1988).

Bishayee et al. "Characterization of a Novel Anti-Peptide Antibody that Recognizes a Specific Conformation of the Platelet-Derived Growth Factor Receptor" *Mol. And Cell. Biol.* 8(9):3696-3702 (Sep. 1988).

Claesson-Welsh et al. "Biosynthesis and intracellular transport of the receptor for platelet-derived growth factor" *Proc. Natl. Acad. Sci. USA* 84: 8796-8800 (Dec. 1987).

New England Biolabs Catalog (Published by New England Biolabs, Beverly, Massachusetts), pp. 60-62 (1986/1987).

Kruh et al. "A Novel Human Gene Closely Related to the *ab7* Proto-Oncogene" *Science* 234:1545-1548 (Dec. 19, 1986).

Morrison et al. "Chimeric human antibody molecules: Mouse antigen-binding domains with human constant region domains" *Proc. Natl. Acad. Sci. USA* 81: 6851-6855 (Nov. 1984).

Raines et al. "Platelet-derived Growth Factor" *Journal of Biological Chemistry* 257(9): 5154-5160 (May 10, 1982).

Genzyme Diagnostics, Research Products Catalog p. 152 "Monoclonal Mouse Anti-Human PDGF R α-Subunit" and "Monoclonal Mouse Anti-Human PDGF R β-Subunit" (1997).

Yarden et al., "Structure of the Receptor For Platelet-Derived Growth Factor Helps Define A Family Of Closely Related Growth Factor Receptors", *Nature*, vol. 323:226-32, (1986).

Kruh et al., "A Novel Gene Closely Related to the *abl* proto-Oncogene", *Science*, 234: 1545-1548 (1986).

King et al., "Amplification of A Novel v-*erb*B-Related Gene in a Human Mammary Carcinoma", *Science*, 229: 974-976 (1986).

Claesson-Welsh et al., "cDNA Cloning and Expression of a Human A-Type Platelet-Derived Growth Factor (PDGF) Receptor Establishes Structural Similarity to the B-Type PDGF Receptor," *PNAS, (USA)*, 88(13): 4917-4921 (1988).

Heldin et al., "Binding of Different Forms of PDGF Receptors To Human Fibroblasts; Evidence for Two Receptor Types," *EMBO*, 7(5): 1387-1393 (1988).

Hart et al. "Synthesis, Phosphorylation, and Degradation of Multiple Forms of the Platelet-derived Growth Factor Receptor Studied Using a Monoclonal Antibody," *J. Biol. Chem.* 262(22): 10780-10785 (1987).

Kawahara et al. "Monoclonal Antibody C3.1 is a Platelet Derived Growth Factor (PDGF) Antagonist," *Biochem. Biophys. Res. Comm.*, 147(2); 839-845 (1987).

Claesson-Welsh et al. cDNA Cloning and Expression of the Human A-type Platelet-Derived Growth Factor-(PDGF) Receptor Establishes Structural Similarity to the B-type PDGF Receptor, *Proc. Natl. Acad. Sci, USA*, 86: 4917-4921 (1987).

Nister et al. "Expression of Messenger RNAs for Platelet-derived Growth Factor and Transforming Growth Factor-$\alpha$ and Their Receptors in Human Malignant Glioma Cell Lines," *Can. Res.*, 48: 3910-3918 (1988).

Escobedo et al. A common PDGF Receptor is Activated by Homodimeric A and B Forms of PDGF, *Science*, 240: 1532-1534.

Johnsson Platelet-Derived Growth Factor: Identification of Constitutent Polypeptide Chains, *Biochem. Biophys. Res. Comm.*, 104(1): 66-74 (1982).

Gronwald et al. Cloning and Expression of a cDNA Coding for the Human Platelet-Derived Growth Factor Receptor: Evidence For More Than One Receptor Class, *Proc. Natl. Acad. Sci. USA*, 85: 3435-3439 (1988).

* cited by examiner

FIG. 3-1

```
  1 CCATTACTGTTGGAGCTACAGGGAGAGAAACAGGAGGAGACTGCAAGAGA

49 TCATTTGGGAAGGCCGTGGGCACGCTCTTTACTCCATGTGTGGGACATT

MetGly
100 CATTGCGGAATAACATCGGAGGAGAAGTTTCCCAGAGCTATGGGG 5                10               15
      ThrSerHisProAlaPheLeuValLeuGlyCysLeuLeuThrGly
145 ACTTCCCATCCGGCGTTCCTGGTCTTAGGCTGTCTTCTCACAGG 20                25               30
      LeuSerLeuIleLeuCysGlnLeuSerLeuProSerIleLeuPro
190 CTGAGCCTAATCCTCTGCCAGCTTTCATTACCCTCTATCCTTCCA 35                40               45
      AsnGluAsnGluLysValValGlnLeuAsnSerSerPheSerLeu
235 AATGAAAATGAAAAGGTTGTGCAGCTGAATTCATCCTTTTCTCTG 50                55               60
      ArgCysPheGlyGluSerGluValSerTrpGlnTyrProMetSer
280 AGATGCTTTGGGGAGAGTGAAGTGAGCTGGCAGTACCCCATGTCT 65                70               75
      GluGluGluSerSerAspValGluIleArgAsnGluGluAsnAsn
325 GAAGAAGAGAGCTCCGATGTGGAAATCAGAAATGAAGAAAACAAC 80                85               90
      SerGlyLeuPheValThrValLeuGluValSerSerAlaSerAla
370 AGCGGCCTTTTTGTGACGGTCTTGGAAGTGAGCAGTGCCTCGGCG 95               100              105
      AlaHisThrGlyLeuTyrThrCysTyrTyrAsnHisThrGlnThr
415 GCCCACACAGGGTTGTACACTTGCTATTACAACCACACTCAGACA 110               115              120
      GluGluAsnGluLeuGluGlyArgHisIleTyrIleTyrValPro
460 GAAGAGAATGAGCTTGAAGGCAGGCACATTTACATCTATGTGCCA 125               130              135
      AspProAspValAlaPheValProLeuGlyMetThrAspTyrLeu
505 GACCCAGATGTAGCCTTTGTACCTCTAGGAATGACGGATTATTTA
```

FIG. 3-2

```
              140              145              150
      ValIleValGluAspAspAspSerAlaIleIleProCysArgThr
550   GTCATCGTGGAGGATGATGATTCTGCCATTATACCTTGTCGCACA 155              160              165
      ThrAspProGluThrProValThrLeuHisAsnSerGluGlyVal
595   ACTGATCCCGAGACTCCTGTAACCTTACACAACAGTGAGGGGGTG 170              175              180
      ValProAlaSerTyrAspSerArgGlnGlyPheAsnGlyThrPhe
640   GTACCTGCCTCCTACGACAGCAGACAGGGCTTTAATGGGACCTTC 185              190              195
      ThrValGlyProTyrIleCysGluAlaThrValLysGlyLysLys
685   ACTGTAGGGCCCTATATCTGTGAGGCCACCGTCAAAGGAAAGAAG 200              205              210
      PheGlnThrIleProPheAsnValTyrAlaLeuLysAlaThrSer
730   TTCCAGACCATCCCATTTAATGTTTATGCTTTAAAAGCAACATCA 215              220              225
      GluLeuAspLeuGluMetGluAlaLeuLysThrValTyrLysSer
775   GAGCTGGATCTAGAAATGGAAGCTCTTAAAACCGTGTATAAGTCA 230              235              240
      GlyGluThrIleValValThrCysAlaValPheAsnAsnGluVal
820   GGGGAAACGATTGTGGTCACCTGTGCTGTTTTTAACAATGAGGTG 245              250              255
      ValAspLeuGlnTrpThrTyrProGlyGluValLysGlyLysGly
865   GTTGACCTTCAATGGACTTACCCTGGAGAAGTGAAAGGCAAAGGC 260              265              270
      IleThrMetLeuGluGluIleLysValProSerIleLysLeuVal
910   ATCACAATGCTGGAAGAAATCAAAGTCCCATCCATCAAATTGGTG 275              280              285
      TyrThrLeuThrValProGluAlaThrValLysAspSerGlyAsp
955   TACACTTTGACGGTCCCCGAGGCCACGGTGAAAGACAGTGGAGAT 290              295              300
      TyrGluCysAlaAlaArgGlnAlaThrArgGluValLysGluMet
1000  TACGAATGTGCTGCCCGCCAGGCTACCAGGGAGGTCAAAGAAATG 305              310              315
      LysLysValThrIleSerValHisGluLysGlyPheIleGluIle
1045  AAGAAAGTCACTATTTCTGTCCATGAGAAAGGTTTCATTGAAATC
```

FIG. 3-3

```
              320                 325                 330
        LysProThrPheSerGlnLeuGluAlaValAsnLeuHisGluVal
1090    AAACCCACCTTCAGCCAGTTGGAAGCTGTCAACCTGCATGAAGTC 335                 340                 345
        LysHisPheValValGluValArgAlaTyrProProProArgIle
1135    AAACATTTTGTTGTAGAGGTGCGGGCCTACCCACCTCCCAGGATA 350                 355                 360
        SerTrpLeuLysAsnAsnLeuThrLeuIleGluAsnLeuThrGlu
1180    TCCTGGCTGAAAAACAATCTGACTCTGATTGAAAATCTCACTGAG 365                 370                 375
        IleThrThrAspValGluLysIleGlnGluIleArgTyrArgSer
1225    ATCACCACTGATGTGGAAAAGATTCAGGAAATAAGGTATCGAAGC 380                 385                 390
        LysLeuLysLeuIleArgAlaLysGluGluAspSerGlyHisTyr
1270    AAATTAAAGCTGATCCGTGCTAAGGAAGAAGACAGTGGCCATTAT 395                 400                 405
        ThrIleValAlaGlnAsnGluAspAlaValLysSerTyrThrPhe
1315    ACTATTGTAGCTCAAAATGAAGATGCTGTGAAGAGCTATACTTTT 410                 415                 420
        GluLeuLeuThrGlnValProSerSerIleLeuAspLeuValAsp
1360    GAACTGTTAACTCAAGTTCCTTCATCCATTCTGGACTTGGTCGAT 425                 430                 435
        AspHisHisGlySerThrGlyGlyGlnThrValArgCysThrAla
1405    GATCACCATGGCTCAACTGGGGGACAGACGGTGAGGTGCACAGCT 440                 445                 450
        GluGlyThrProLeuProAspIleGluTrpMetIleCysLysAsp
1450    GAAGGCACGCCGCTTCCTGATATTGAGTGGATGATATGCAAAGAT 455                 460                 465
        IleLysLysCysAsnAsnGluThrSerTrpThrIleLeuAlaAsn
1495    ATTAAGAAATGTAATAATGAAACTTCCTGGACTATTTTGGCCAAC 470                 475                 480
        AsnValSerAsnIleIleThrGluIleHisSerArgAspArgSer
1540    AATGTCTCAAACATCATCACGGAGATCCACTCCCGAGACAGGAGT 485                 490                 495
        ThrValGluGlyArgValThrPheAlaLysValGluGluThrIle
1585    ACCGTGGAGGGCCGTGTGACTTTCGCCAAAGTGGAGGAGACCATC
```

FIG. 3-4

```
             500                505                510
    AlaValArgCysLeuAlaLysAsnLeuLeuGlyAlaGluAsnArg
1630 GCCGTGCGATGCCTGGCTAAGAATCTCCTTGGAGCTGAGAACCGA 515                520                525
       GluLeuLysLeuValAlaProThrLeuArgSerGluLeuThrVal
1675 GAGCTGAAGCTGGTGGCTCCCACCCTGCGTTCTGAACTCACGGTG 530                535                540
       AlaAlaAlaValLeuValLeuLeuValIleValIleIleSerLeu
1720 GCTGCTGCAGTCCTGGTGCTGTTGGTGATTGTGATCATCTCACTT 545                550                555
       IleValLeuValValIleTrpLysGlnLysProArgTyrGluIle
1765 ATTGTCCTGGTTGTCATTTGGAAACAGAAACCGAGGTATGAAATT 560                565                570
       ArgTrpArgValIleGluSerIleSerProAspGlyHisGluTyr
1810 CGCTGGAGGGTCATTGAATCAATCAGCCCGGATGGACATGAATAT 575                580                585
       IleTyrValAspProMetGlnLeuProTyrAspSerArgTrpGlu
1855 ATTTATGTGGACCCGATGCAGCTGCCTTATGACTCAAGATGGGAG 590                595                600  •
       PheProArgAspGlyLeuValLeuGlyArgValLeuGlySerGly
1900 TTTCCAAGAGATGGACTAGTGCTTGGTCGGGTCTTGGGGTCTGGA 605                610                615
       AlaPheGlyLysValValGluGlyThrAlaTyrGlyLeuSerArg
1945 GCGTTTGGGAAGGTGGTTGAAGGAACAGCCTATGGATTAAGCCGG 620                625       •        630
       SerGlnProValMetLysValAlaValLysMetLeuLysProThr
1990 TCCCAACCTGTCATGAAAGTTGCAGTGAAGATGCTAAAACCCACG 635                640                645
       AlaArgSerSerGluLysGlnAlaLeuMetSerGluLeuLysIle
2035 GCCAGATCCAGTGAAAAACAAGCTCTCATGTCTGAACTGAAGATA 650                655                660
       MetThrHisLeuGlyProHisLeuAsnIleValAsnLeuLeuGly
2080 ATGACTCACCTGGGGCCACATTTGAACATTGTAAACTTGCTGGGA 665                670                675
       AlaCysThrLysSerGlyProIleTyrIleIleThrGluTyrCys·
2125 GCCTGCACCAAGTCAGGCCCCATTTACATCATCACAGAGTATTGC
```

FIG. 3-5

```
             680              685              690
        PheTyrGlyAspLeuValAsnTyrLeuHisLysAsnArgAspSer
2170    TTCTATGGAGATTTGGTCAACTATTTGCATAAGAATAGGGATAGC 695              700              705
        PheLeuSerHisHisProGluLysProLysLysGluLeuAspIle
2215    TTCCTGAGCCACCACCCAGAGAAGCCAAAGAAAGAGCTGGATATC 710              715              720
        PheGlyLeuAsnProAlaAspGluSerThrArgSerTyrValIle
2260    TTTGGATTGAACCCTGCTGATGAAAGCACACGGAGCTATGTTATT 725              730              735
        LeuSerPheGluAsnAsnGlyAspTyrMetAspMetLysGlnAla
2305    TTATCTTTTGAAAACAATGGTGACTACATGGACATGAAGCAGGCT 740              745              750
        AspThrThrGlnTyrValProMetLeuGluArgLysGluValSer
2350    GATACTACACAGTATGTCCCCATGCTAGAAAGGAAAGAGGTTTCT 755              760              765
        LysTyrSerAspIleGlnArgSerLeuTyrAspArgProAlaSer
2395    AAATATTCCGACATCCAGAGATCACTCTATGATCGTCCAGCCTCA 770              775              780
        TyrLysLysLysSerMetLeuAspSerGluValLysAsnLeuLeu
2440    TATAAGAAGAAATCTATGTTAGACTCAGAAGTCAAAAACCTCCTT 785              790              795
        SerAspAspAsnSerGluGlyLeuThrLeuLeuAspLeuLeuSer
2485    TCAGATGATAACTCAGAAGGCCTTACTTTATTGGATTTGTTGAGC 800              805              810
        PheThrTyrGlnValAlaArgGlyMetGluPheLeuAlaSerLys
2530    TTCACCTATCAAGTTGCCCGAGGAATGGAGTTTTTGGCTTCAAAA 815              820              825
        AsnCysValHisArgAspLeuAlaAlaArgAsnValLeuLeuAla
2575    AATTGTGTCCACCGTGATCTGGCTGCTCGCAACGTCCTCCTGGCA 830              835              840
        GlnGlyLysIleValLysIleCysAspPheGlyLeuAlaArgAsp
2620    CAAGGAAAAATTGTGAAGATCTGTGACTTTGGCCTGGCCAGAGAC 845              850              855
        IleMetHisAspSerAsnTyrValSerLysGlySerThrPheLeu
2665    ATCATGCATGATTCGAACTATGTGTCGAAAGGCAGTACCTTTCTG
```

FIG. 3-6

```
            860              865              870
       ProValLysTrpMetAlaProGluSerIlePheAspAsnLeuTyr
2710   CCCGTGAAGTGGATGGCTCCTGAGAGCATCTTTGACAACCTCTAC
                         [a]

875              880              885
       ThrThrLeuSerAspValTrpSerTyrGlyIleLeuLeuTrpGlu
2755   ACCACACTGAGTGATGTCTGGTCTTATGGCATTCTGCTCTGGGAG 890              895              900
       IlePheSerLeuGlyGlyThrProTyrProGlyMetMetValAsp
2800   ATCTTTTCCTTGGTGGCACCCCTTACCCCGGCATGATGGTGGAT
                       /\

905              910              915
       SerThrPheTyrAsnLysIleLysSerGlyTyrArgMetAlaLys
2845   TCTACTTTCTACAATAAGATCAAGAGTGGGTACCGGATGGCCAAG
       [b]

920              925              930
       ProAspHisAlaThrSerGluValTyrGluIleMetValLysCys
2890   CCTGACCACGCTACCAGTGAAGTCTACGAGATCATGGTGAAATGC
                            /\

935              940              945
       TrpAsnSerGluProGluLysArgProSerPheTyrHisLeuSer
2935   TGGAACAGTGAGCCGGAGAAGAGACCCTCCTTTTACCACCTGAGT
                       [c]

950              955              960
       GluIleValGluAsnLeuLeuProGlyGlnTyrLysLysSerTyr
2980   GAGATTGTGGAGAATCTGCTGCCTGGACAATATAAAAGAGTTAT
                                            /

965              970              975
       GluLysIleHisLeuAspPheLeuLysSerAspHisProAlaVal
3025   GAAAAAATTCACCTGGACTTCCTGAAGAGTGACCATCCTGCTGTG 980              985              990
       AlaArgMetArgValAspSerAspAsnAlaTyrIleGlyValThr
3070   GCACGCATGCGTGTGGACTCAGACAATGCATACATTGGTGTCACC 995             1000             1005
       TyrLysAsnGluGluAspLysLeuLysAspTrpGluGlyGlyLeu
3115   TACAAAAACGAGGAAGACAAGCTGAAGGACTGGGAGGGTGGTCTG
```

FIG. 3-7

```
                1010              1015              1020
          AspGluGlnArgLeuSerAlaAspSerGlyTyrIleIleProLeu
3160 GATGAGCAGAGACTGAGCGCTGACAGTGGCTACATCATTCCTCTG 1025              1030              1035
          ProAspIleAspProValProGluGluGluAspLeuGlyLysArg
3205 CCTGACATTGACCCTGTCCCTGAGGAGGAGGACCTGGGCAAGAGG 1040              1045              1050
          AsnArgHisSerSerGlnThrSerGluGluSerAlaIleGluThr
3250 AACAGACACAGCTCGCAGACCTCTGAAGAGAGTGCCATTGAGACG 1055              1060              1065
          GlySerSerSerThrPheIleLysArgGluAspGluThrIle
3295 GGTTCCAGCAGTTCCACCTTCATCAAGAGAGAGGACGAGACCATT 1070              1075              1080
          GluAspIleAspMetMetAspAspIleGlyIleAspSerSerAsp
3340 GAAGACATCGACATGATGGACGACATCGGCATAGACTCTTCAGAC

1085
          LeuValGluAspSerPheLeu
3385 CTGGTGGAAGACAGCTTCCTGTAACTGGCGGATTCGAGGGGTTCC

3430 TTCCACTTCTGGGGCCACCTCTGGATCCCGTTCAGAAAACCACTT

3475 TATTGCAATGCGGAGGTTGAGAGGAGGACTTGGTTGATGTTTAAA

3520 GAGAAGTTCCCAGCCAAGGGCCTCGGGGAGCGTTCTAAATATGAA

3565 TGAATGGGATATTTTGAAATGAACTTTGTCAGTGTTGCCTCTCGC

3610 AATGCCTCAGTAGCATCTCAGTGGTGTGTGAAGTTTGGAGATAGA

3655 TGGATAAGGGAATAATAGGCCACAGAAGGTGAACTTTGTGCTTCA

3700 AGGACATTGGTGAGAGTCCAACAGACACAATTTATACTGCGACAG

3745 AACTTCAGCATTGTAATTATGTAAATAACTCTAACCAAGGCTGTG

3790 TTTAGATTGTATTAACTATCTTCTTTGGACTTCTGAAGAGACCAC

3835 TCAATCCATCCATGTACTTCCCTCTTGAAACCTGATGTCAGCTGC

3880 TGTTGAACTTTTTAAAGAAGTGCATGAAAAACCATTTTTGAACCT

3925 TAAAAGGTACTGGTACTATAGCATTTTGCTATCTTTTTTAGTGTT
```

FIG. 3-8

```
3970  AAGAGATAAAGAATAATAATTAACCAACCTTGTTTAATAGATTTG
4015  GGTCATTTAGAAGCCTGACAACTCATTTTCATATTGTAATCTATG
4060  TTTATAATACTACTACTGTTATCAGTAATGCTAAATGTGTAATAA
4105  TGTAACATGATTTCCCTCCAGAGAAAGCACAATTTAAAACAATCC
4150  TTACTAAGTAGGTGATGAGTTTGACAGTTTTGACATTTATATTA
4195  AATAACATGTTTCTCTATAAGTATGGTAATAGCTTTAGTGAATT
4240  AAATTTAGTTGAGCATAGAGAACAAAGTAAAAGTAGTGTTGTCCA
4285  GGAAGTCAGAATTTTTAACTGTACTGAATAGGTTCCCCAATCCAT
4330  CGTATTAAAAAACAATTAACTGCCCTCTGAAATAATGGGATTAGA
4375  AACAAACAAAACTCTTAAGTCCTAAAAGTTCTCAATGTAGAGGCA
4420  TAAACCTGTGCTGAACATAACTTCTCATGTATATTACCCAATGGA
4465  AAATATAATGATCAGCAAAAGACTGGATTTGCAGAAGTTTTTTT
4510  TTTTTTTCTTCATGCCTGATGAAAGCTTTGGCAACCCCAATATAT
4555  GTATTTTTTGAATCTATGAACCTGAAAAGGGTCAGAAGGATGCCC
4600  AGACATCAGCCTCCTTCTTTCACCCCTTACCCCAAAGAGAAAGAG
4645  TTTGAAACTCGAGACCATAAAGATATTCTTTAGTGGAGGCTGGAT
4690  GTGCATTAGCCTGGATCCTCAGTTCTCAAATGTGTGTGGCAGCCA
4735  GGATGACTAGATCCTGGGTTTCCATCCTTGAGATTCTGAAGTATG
4780  AAGTCTGAGGGAAACCAGAGTCTGTATTTTTCTAAACTCCCTGGC
4825  TGTTCTGATCGGCCAGTTTTCGGAAACACTGACTTAGGTTTCAGG
4870  AAGTTGCCATGGGAAACAAATAATTTGAACTTTGGAACAGGGTTG
4915  GAATTCAACCACGCAGGAAGCCTACTATTTAAATCCTTGGCTTCA
4960  GGTTAGTGACATTTAATGCCATCTAGCTAGCAATTGCGACCTTAA
5005  TTTAACTTTCCAGTCTTAGCTGAGGCTGAGAAAGCTAAAGTTTGG
```

FIG. 3-9

```
5050 TTTTGACAGGTTTTCCAAAAGTAAAGATGCTACTTCCCACTGTAT
5095 GGGGGAGATTGAACTTTCCCCGTCTCCGTCTTCTGCCTCCCACT
5140 CCATACCCCGCCAAGGAAAGGCATGTACAAAAATTATGCAATTCA
5185 GTGTTCCAAGTCTCTGTGTAACCAGCTCAGTGTTTTGGTGGAAAA
5230 AACATTTTAAGTTTTACTGATAATTTGAGGTTAGATGGGAGGATG
5275 AATTGTCACATCTATCCACACTGTCAAACAGGTTGGTGTGGGTTC
5320 ATTGGCATTCTTTGCAATACTGCTTAATTGCTGATACCATATGAA
5365 TGAAACATGGGCTGTGATTACTGCAATCACTGTGCTATCGGCAGA
5410 TGATGCTTTGGAAGATGCAGAAGCAATAATAAAGTACTTGACTAC
5455 CTACTGGTGTAATCTCAATGCAAGCCCCAACTTTCTTATCCAACT
5500 TTTTCATAGTAAGTGCGAAGACTGAGCCAGATTGGCCAATTAAAA
5545 ACGAAACCTGACTAGGTTCTGTAGAGCCAATTAGACTTGAAATA
5590 CGTTTGTGTTTCTAGAATCACAGCTCAAGCATTCTGTTTATCGCT
5635 CACTCTCCCTTGTACAGCCTTATTTTGTTGGTGCTTTGCATTTTG
5680 ATATTGCTGTGAGCCTTGCATGACATCATGAGGCCGGATGAAACT
5725 TCTCAGTCCAGCAGTTTCCAGTCCTAACAAATGCTCCCACCTGAA
5770 TTTGTATATGACTGCATTTGTGGGTGTGTGTGTTTTCAGCAAA
5815 TTCCAGATTTGTTTCCTTTTGGCCTCCTGCAAAGTCTCCAGAAGA
5860 AAATTTGCCAATCTTTCCTACTTTCTATTTTATGATGACAATCA
5905 AAGCCGGCCTGAGAAACACTATTTGTGACTTTTTAAACGATTAGT
5950 GATGTCCTTAAAATGTGGTCTGCCAATCTGTACAAAATGGTCCTA
5995 TTTTTGTGAAGAGGGACATAAGATAAATGATGTTATACATCAAT
6040 ATGTATATATGTATTTCTATATAGACTTGGAGAATACTGCCAAAA
6085 CATTTATGACAAGCTGTATCACTGCCTTCGTTTATATTTTTTTAA
```

```
6130  CTGTGATAATCCCCACAGGCACATTAACTGTTGCACTTTTGAATG

6175  TCCAAAATTTATATTTTAGAAATAATAAAAGAAAGATACTTACA

6220  TGTTCCCAAAACAATGGTGTGGTGAATGTGTGAGAAAACTAACT

6265  TGATAGGGTCTACCAATACAAATGTATTACGAATGCCCTGTTC

6310  ATGTTTTTGTTTTAAAACGTGTAAATGAAGATCTTTATATTTCAA

6355  TAAATGATATATAATTTAAAGTTAAAAAAAAAAAAAAAAAAAAA

6400  AAAAAAAAAAAAA
```

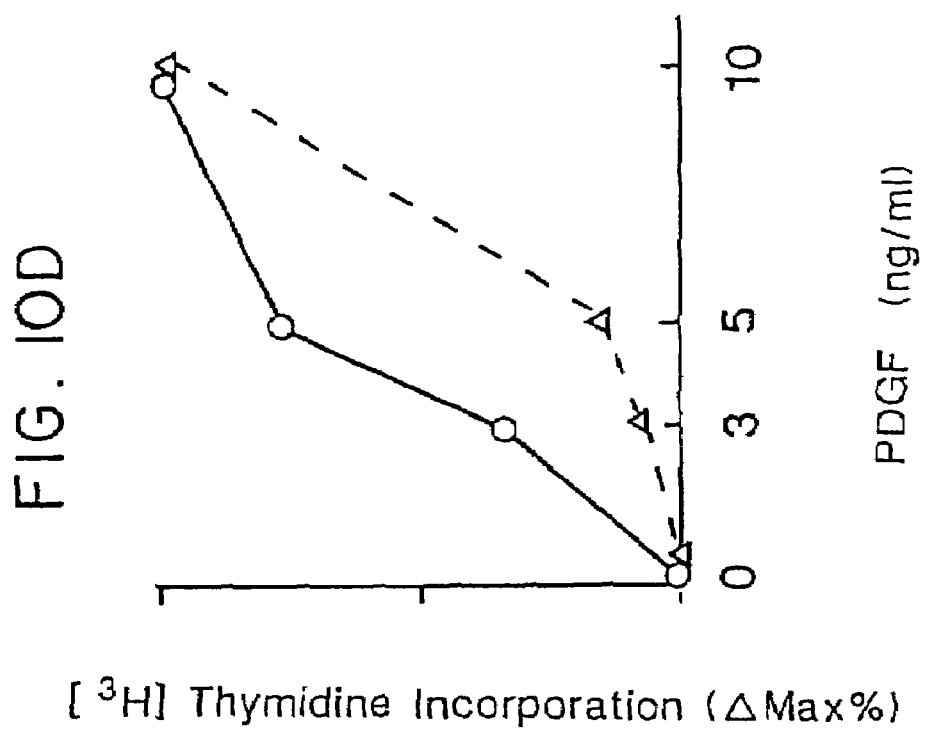
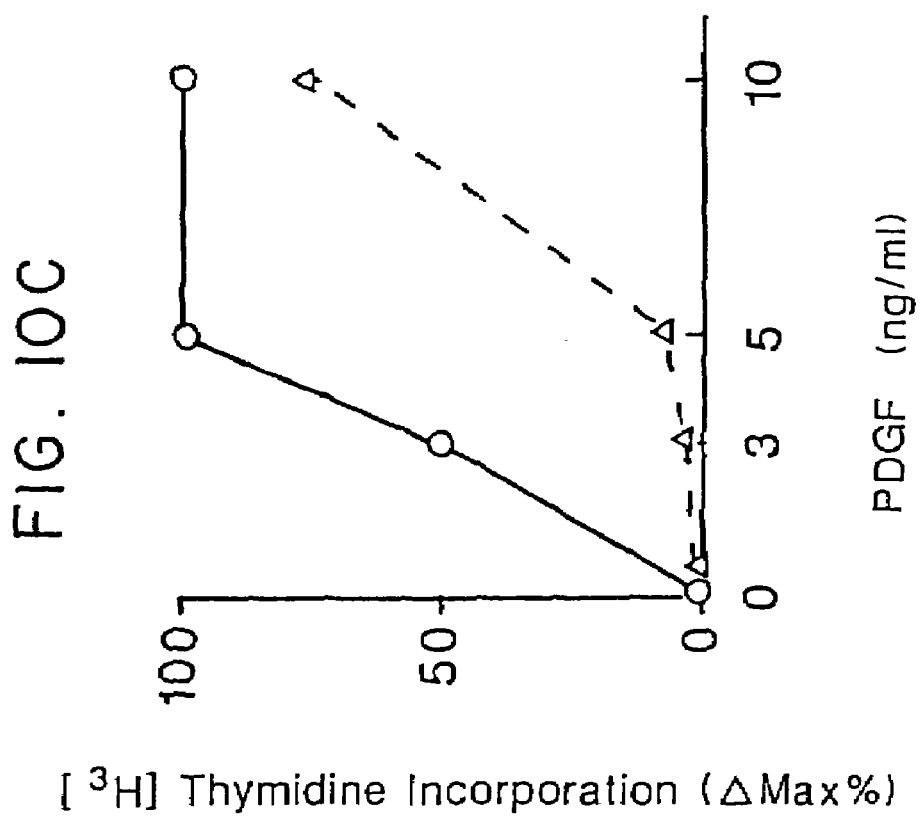

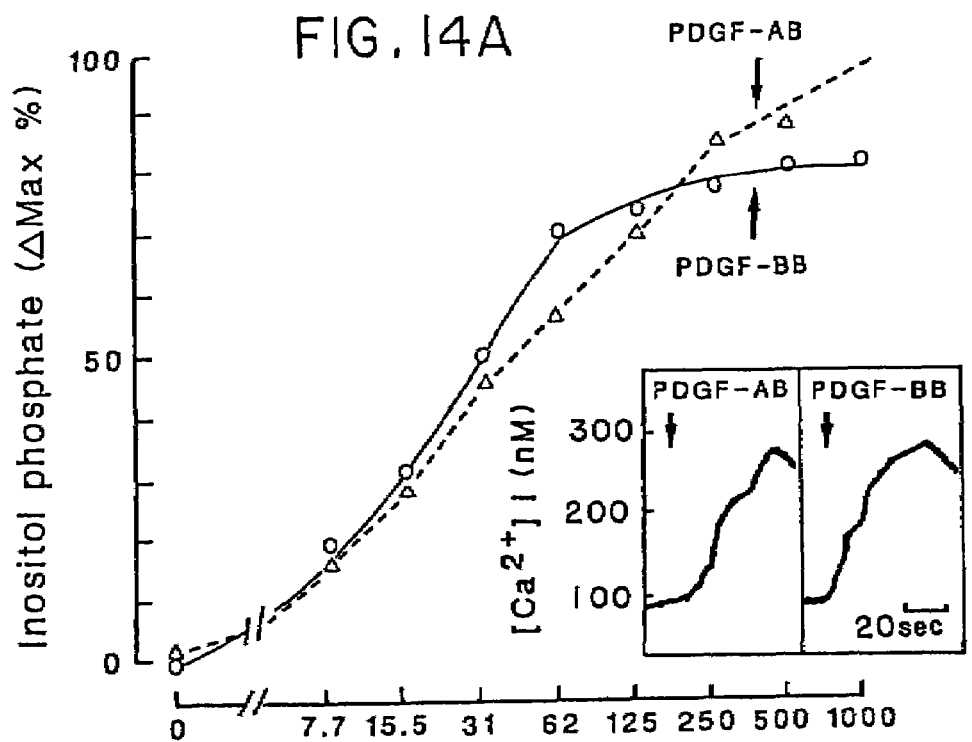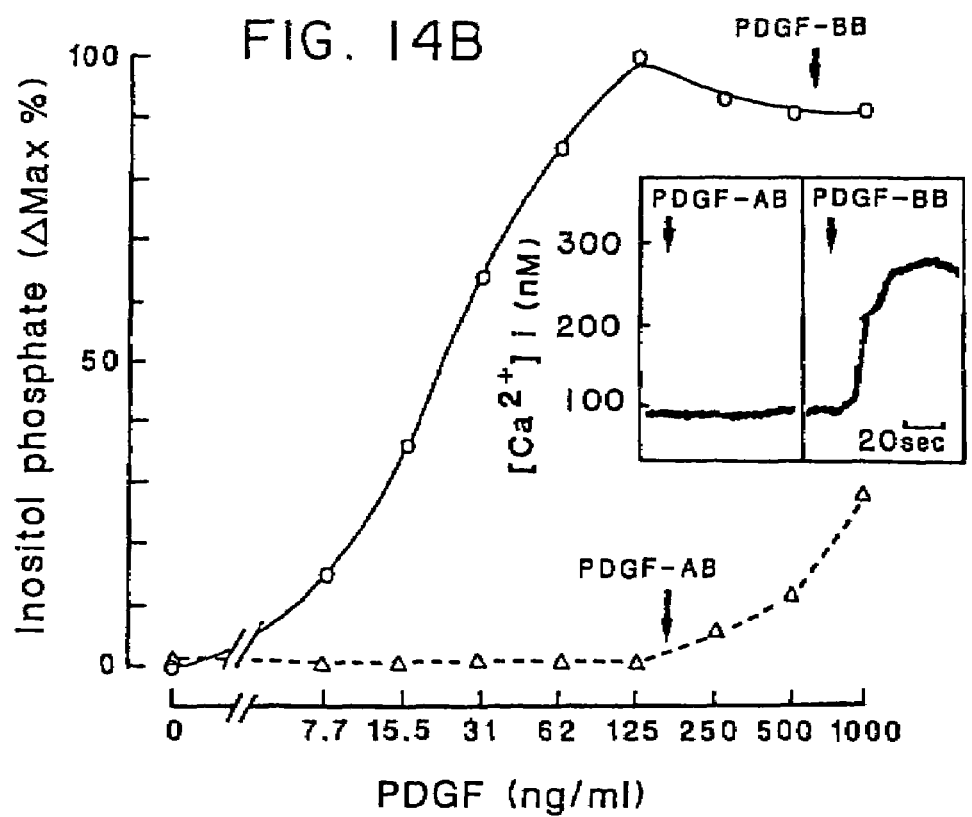

METHODS FOR IDENTIFYING ALPHA PDGFR AGONISTS AND ANTAGONISTS

This application is a continuation of Ser. No. 09/769,987, filed Jan. 25, 2001, now U.S. Pat. No. 6,660,488 (14014.0266U2), now allowed, which is a divisional of Ser. No. 08/460,656, filed Jun. 2, 1995 (14014.0266US), now U.S. Pat. No. 6,228,600, issued May 8, 2001, which is a divisional of 08/439,095, filed May 11, 1995 (14014.0279), pending, which is a continuation of Ser. No. 07/915,884, filed Jul. 20, 1992, abandoned, which is a continuation of Ser. No. 07/308,282, filed Feb. 9, 1989, abandoned. All of these applications are herein incorporated by reference in their entireties.

FIELD OF THE INVENTION

The present invention relates to genes which encode receptor proteins for Platelet Derived Growth Factor (PDGF), particularly to those human genes encoding receptor proteins which preferentially bind the major form of human PDGF which is found in platelets. This invention also relates to synthesis of products of such PDGF receptor genes by recombinant cells, and to the manufacture and use of certain other novel products enabled by the identification and cloning of DNAs encoding these receptors.

BACKGROUND OF THE INVENTION

Genes encoding growth factors and their receptors have been implicated in the regulation of normal cell growth and development. There is also increasing evidence that genetic alterations affecting expression of such genes can contribute to altered cell growth associated with malignancy. The normal homologues of some oncogenes code for membrane-spanning growth factor receptors with tyrosine kinase activity (2, 3). Other oncogenes appear to act in pathways of growth factor activated cell proliferation as well (4). Thus, increased knowledge of growth factor regulatory systems in general is expected to provide better understanding of genes critically involved in both normal growth control and neoplasia.

Platelet-Derived Growth Factor (PDGF) is of particular importance because it is a major connective tissue cell mitogen which is thought to play a major role in normal wound healing. Further, the abnormal expression of PDGF has been implicated not only in cancers, but also in a variety of histopathologic states including arteriosclerosis, arthritis, and fibrotic diseases (23).

PDGF consists of a disulfide-linked dimer of two polypeptide chains, designated A and B. There is evidence for the natural occurrence of all three possible dimeric structures containing A or B chains or both (1, 25, 26). The various dimeric forms of the growth factor are called "isoforms". A variety of normal and neoplastic cells appear to specifically express either the A or B chains. Nevertheless, the most significant human isoform for physiological regulatory processes is believed to be the one isolated from human platelets, namely the AB heterodimer (i.e., a dimer containing one A and one B chain; see reference 24).

The PDGF-A and B chains have distinguishable properties (37). The A chain is much more efficiently secreted and exhibits lower specific mitogenic activity than the B chain. The B chain gene of PDGF has been shown to be the normal human homoloque of the simian sarcoma virus-derived v-sis oncogene. Moreover, there is accumulating evidence that expression of the B chain in cell types possessing PDGF receptors can drive such cells along the pathway to malignancy. The A chain is less potent than the B chain in inducing neoplastic transformation of cultured mouse (NIH/3T3) cells.

Recent studies have suggested the existence of two subtypes of the PDGF receptor (PDGF-R), on the basis of PBGF isoform binding and competition using mouse or human fibroblasts (27). These works are consistent with the hypothesis that there exists one receptor subtype which preferentially binds the B chain dimer, and another which efficiently binds all isoforms of the PDGF molecule. However, the results of these studies could not discriminate between two distinct possibilities with differing implications for the study and ultimate treatment of diseases involving such receptors: either these subtypes represent differently processed products of a single PDGF-R gene; or they are products of distinct genes.

Further, there have been conflicting findings concerning binding of different PDGF isoforms of the receptor produced by a previously identified human PDGF-R gene. Introduction of PDGF-R genes by expression vectors into different cell types devoid of PDGF receptors has been reported to lead either to preferential binding of PDGF-BB (14) or, alternatively, to efficient binding by all three isoforms (28). The basis of this discrepancy is not known.

Thus, there has been uncertainty concerning the ability of the known PDGF receptor to respond to different PDGF isoforms, and to the main AB heterodimer form of human PDGF, in particular. Some reported differences might be explained by cell specific differences in post-translational processing of the product of the known PDGF-R gene, or by the presence of accessory proteins in certain cell types. Alternatively, the different binding properties reported in different studies might be explained by the existence of two distinct genes encoding different PDGF receptors.

In light of the complexities of PDGF ligand and receptor activities described above, and the related processes which are influenced thereby, comprising both normal wound healing and abnormal connective tissue conditions, including neoplastic growth, arteriosclerosis, arthritis, and fibrotic diseases, it is apparent that there has been a need for methods and compositions and bioassays which would provide an improved knowledge and analysis of mechanisms of connective tissue growth regulation, and, ultimately, a need for novel diagnostics and therapies based on the PDGF receptors involved therein.

In particular, the observations above indicate a specific need for thorough characterization of the genetic basis of PDGF receptor production. Furthermore, it has been shown previously (5) that it is possible to identify and clone novel related members of the gene family encoding membrane-spanning growth factor receptors with tyrosine kinase activity, which comprises the known PDGF receptor gene and the kit and fms oncogenes, by exploiting the conserved tyrosine kinase coding region as a probe.

Accordingly, the present invention contemplates the application of methods of recombinant DNA technology to fulfill the above needs and to develop means for producing PDGF receptor proteins which appear to be the predominant effectors of the main form of human PDGF. This invention also contemplates the application of the molecular mechanisms of these receptors related to healing and pathological processes.

In particular, it is an object of the present invention to identify and isolate the coding sequence of a novel human gene related to but distinct from the known PDGF-R gene, as well as from other members of the family of tyrosine kinase genes comprising the PDGF-R, kit, and fms genes. Further, it is an object of this invention to develop the molecular tools needed to establish the relative roles of the novel and known forms of PDGF receptor in physiological processes involving PDGF.

SUMMARY OF THE INVENTION

The present invention relates to a development of recombinant DNA technology, which includes production of novel PDGF receptor (PDGF-R) proteins, free of other peptide factors. Novel DNA segments, RNAs, and bioassay methods are also included.

The present invention in particular relates, in part, to DNA segments which encode messenger RNAs (mRNAs) and proteins having structural and/or functional characteristics of a new human receptor within the subfamily of membrane-spanning tyrosine kinase receptor genes comprising the following known receptor genes: the PDGF-R gene; colony stimulating factor one receptor (CSF1-R) gene (also known as a cellular form of the fms oncogene, c-fms); and a cellular form of the kit oncogene (c-kit) (see references 3, 6, and 7 for background).

More specifically, this invention includes DNA segments containing a genomic DNA sequence or a DNA sequence complementary to the mRNA transcribed from said genomic DNA (i.e., a "cDNA"), with a predicted protein product similar in structure to other receptors of this growth factor receptor subfamily. Among these receptors, the predicted novel gene product exhibits closest sequence homology to the known DGF receptor.

Further, this novel product encoded by DNAs of this invention is coexpressed with the known PDGF receptor gene product in a variety of normal cell types. This protein product can bind to and be functionally activated by PDGF. However, the activities of different PDGF isoforms functionally distinguish the new product, herein designated the type α human PDGF receptor, from that of previously identified genes encoding receptors that can bind PDGF, including the known receptor previously called the PDGF receptor and herein designated as the type β PDGF receptor. Moreover, considerable evidence disclosed herein indicates that this novel gene product, the type α PDGF receptor, is the main effector of activity for the most abundant form of PDGF in the human body.

In the practice of one embodiment of this invention, the DNA segments are capable of being expressed in suitable host cells, thereby producing the novel PDGF receptor proteins. This invention also relates to mRNAs produced as the result of transcription of the sense strands of the DNA segments of this invention. The invention further comprises novel bioassay methods for determining levels of expression in human cells of the mRNAs and proteins produced from the genes related to DNA segments of the invention.

In a principal embodiment, the present invention comprises DNA segments encoding novel PDGF receptors, as exemplified by the following: a clone of genomic normal human thymus DNA, herein designated as the T11 genomic clone; human cDNA clones of cell mRNAs containing sequences contained in T11, designated HF1, HB6, EF17 and TR4; and related DNA segments which can be detected by hybridization to any of the above human DNA segments, which related segments encode receptor genes, wherein said genes do not include previously known PDGF-related receptor genes.

The human gene related to clone T11 are referred to hereinafter as "the T11 gene" and use of the term "T11" as an adjective is intended to include any of the above DNA segments of this invention, absent a specific reference to "the T11 genomic clone".

In another embodiment, this invention relates to a recombinant DNA molecule comprising a vector and a DNA of the present invention. These recombinant molecules are exemplified by molecules comprising genomic or cDNA clones related to the T11 gene and any of the following vector DNAs a bacteriophage λ cloning vector; or an expression vector capable of expressing inserted DNAs in mammalian cells.

In still another embodiment, the invention comprises a cell, preferably a mammalian cell, transformed with a DNA of the invention. Further, the invention comprises cells, including yeast cells and bacterial cells such as those of *E. coli* and *B. subtilis*, transformed with DNAs of the invention. According to another embodiment of the invention, the transforming DNA is capable of being expressed in the cell, thereby increasing the amount of PDGF-R protein encoded by this DNA, in the cell.

Still further, the invention comprises novel PDGF-R proteins made by expression of a DNA of the invention, or by translation of an RNA of the invention. These receptors can be used for functional studies, and can be purified for additional biochemical and functional analyses, such as qualitative and quantitative receptor binding assays. In particular, these type α PDGF receptors may be used for the development of therapies for conditions involving abnormal processes involving PDGF and its receptors, by testing receptor binding and activation activities of potential analogs (either antagonists or agonists) of the various PDGF isoforms, including the main form of human PDGF.

According to this aspect of the invention, the novel PDGF-R proteins can be protein products of "unmodified" DNAs and mRNAs of the invention, or they can be modified or genetically engineered protein products. As a result of engineered mutations in the DNA sequences, modified PDGF-R proteins have one or more differences in amino acid sequence from the corresponding naturally occurring "wild-type" proteins. These differences may impart functional differences to the modified gene products such as improvements in their manufacturability or suitability for use in bioassays.

This invention also relates to novel bioassay methods for detecting the expression of genes related to DNAs of the invention. According to one such embodiment, DNAs of this invention, particularly the most preferred DNAs, may be used as probes to determine specific levels of mRNAs related to type α PDGF receptors, without interference from mRNAs of known PDGF receptor genes. Such bioassays may be useful, for example, for identification of various classes of tumor cells or of genetic defects in connective tissue growth and/or the healing response.

This invention further comprises novel antibodies made against a peptide encoded by a DNA segment of the invention or by a related DNA. In this embodiment of the invention, the antibodies are monoclonal or polyclonal in origin, and are generated using PDGF receptor-related polypeptides from natural, recombinant or synthetic chemistry sources. These antibodies specifically bind to a PDGF-R protein which includes the sequence of such polypeptide. Preferably, these antibodies bind only to type α PDGF receptor proteins or, alternatively, only to type α PDGF receptor proteins. Also, preferred antibodies of this invention bind to a PDGF receptor protein when that protein is in its native (biologically active) conformation.

Fragments of antibodies of this invention, such as Fab or F(ab)' fragments, which retain antigen binding activity and can be prepared by methods well known in the art, also fall within the scope of the present invention. Further, this invention comprises pharmaceutical compositions of the antibodies of this invention, or active fragments thereof, which can be prepared using materials and methods for preparing pharmaceutical compositions for administration of polypeptides that are well known in the art and can be adapted readily for administration of the present antibodies without undue experimentation.

These antibodies, and active fragments thereof, can be used, for example, for specific detection or purification of either the novel type α PDGF receptor, or, alternatively, of the known type β PDGF receptor. Such antibodies could also be used in various methods known in the art for targeting drugs to tissues with high levels of PDGF receptors, for example, in the treatment of appropriate tumors with conjugates of such antibodies and cell killing agents.

BRIEF DESCRIPTION OF THE FIGURES

FIG. 1 illustrates detection of gene fragments related to the oncogene v-fms and to the known mouse PDGF receptor in human placenta and thymus DNAs by Southern blot hybridization analyses.

FIG. 2 presents the restriction map of the novel v-fms-related gene (T11) and related human PDGF receptor cDNA clones.

FIG. 3 T11 cDNA nucleotide and predicted amino acid sequences. Nucleotides are numbered at the left. The predicted amino acid sequence of the long open reading frame is shown above the nucleotide sequence. Amino acids are numbered over the amino acids, starting at the putative initiation codon. The potential N-terminal signal sequence is underlined. Potential sites of N-linked glycosylation are overlined, and cysteine residues are boxed. The putative single transmembrane region is indicated by a shaded bar. The potential ATP binding site in the kinase domain is indicated by circles over Gly at residues 600, 602 and 605 and Lys at residue 627. The putative tyrosine autophosphorylation site at residue 849 is indicated by *. The regions of the λT11 genomic sequence defined by exons a, b and c are underlined. The AATAAA box close to the polyadenylated 3' end of the cDNA is underlined as well. FIG. 3 contains the nucleotide sequence and deduced amino acid sequence of the novel type α PDGF receptor encoded by the T11 gene.

FIG. 4 depicts results of hydrophobicity analysis of human type α PDGF receptor and homologies of deduced amino acid sequences in comparison with the known type β PDGF receptor and other receptors.

(A) Distribution of silver grains on normal human chromosomes by in situ hybridization with pT11-P probe (clone of the 3.6-kbp PstI genomic fragment) (see FIG. 1). (B) Distribution of grains on chromosome 4. FIG. 5 shows chromosome mapping of the type α PDGF receptor gene.

FIG. 6 is a comparison of mRNA species produced from the type α and β PDGF receptor genes.

FIG. 7 demonstrates specific detection of type α or type β proteins with peptide antisera in human cell lines or in monkey (COS-1) cells transformed with a T11 DNA in an expression vector.

FIG. 8 displays binding Of ($^{125}$ I-labeled) human PDGF to mouse cells (NIH/3T3), control COS-1 cells and COS-1 cells transformed with T11 or known PDGF-R cDNA expression vectors.

FIG. 9 demonstrates tyrosine autophosphorylation of type α and type β PDGF receptors in response to various isoforms of PDGF.

FIG. 10 shows preferential stimulation of DNA synthesis by PDGF isoform, AB in various cells with higher levels of type α PDGF receptor than type β receptor.

FIG. 11 presents binding data for type α and type β PDGF receptors on (human 32D) cells transfected with vectors bearing the respective cDNAs, demonstrating that the type β receptor shows a strikingly lower affinity for the PDGF-AB form.

FIG. 12 illustrates the similar mitogenic responses to PDGF-BB by cells containing either type α or type β PDGF-R and the significantly lesser DNA synthesis response to PDGF-AB in the type β, compared to type α receptor containing cells.

FIG. 13 demonstrates equivalent chemotaxic cellular responses to PDGF-BB in cells with type α or β PDGF-R, whereas PDGF-AB elicited a considerably lower chemotaxic response with type β receptors than with type α receptors.

FIG. 14 Responses of inositol phosphate formation and cytosolic calcium ion mobilization (i.e., $[Ca^2]i$; data in insets) to PDGF-AB (triangles) or PDGF-BB (circles) by human D32 cells reconstituted with type α (upper panel) or type β (lower panel) PDGF receptors. FIG. 14 shows the effect of PDGF-AB and PDGF-BB on inositol phosphate formation and cytosolic calcium mobilization ($[Ca^{2}+]i$) in cells bearing type α and type β PDGF-R, with the type β receptors again responding more efficiently to PDGF-AB.

DESCRIPTION OF SPECIFIC EMBODIMENTS

The DNAs of this invention are exemplified by DNAs referred to herein as: the T11 genomic clone; and clones HF1, HB6, EF17 and TR4, comprising human cDNA clones of cell mRNAs containing sequences included in the T11 genomic clone.

The T11 genomic clone and the TR4 cDNA clone are preferred DNAs of this invention. A clone designated pT11-HP (a HindIII-PstI 0.95-kbp fragment of genomic clone T11) and a particular restriction fragment from a T11 cDNA (3.5-kbp BamHI fragment of TR4, including the whole coding region) are most preferred DNAs of this invention.

Figure 2:
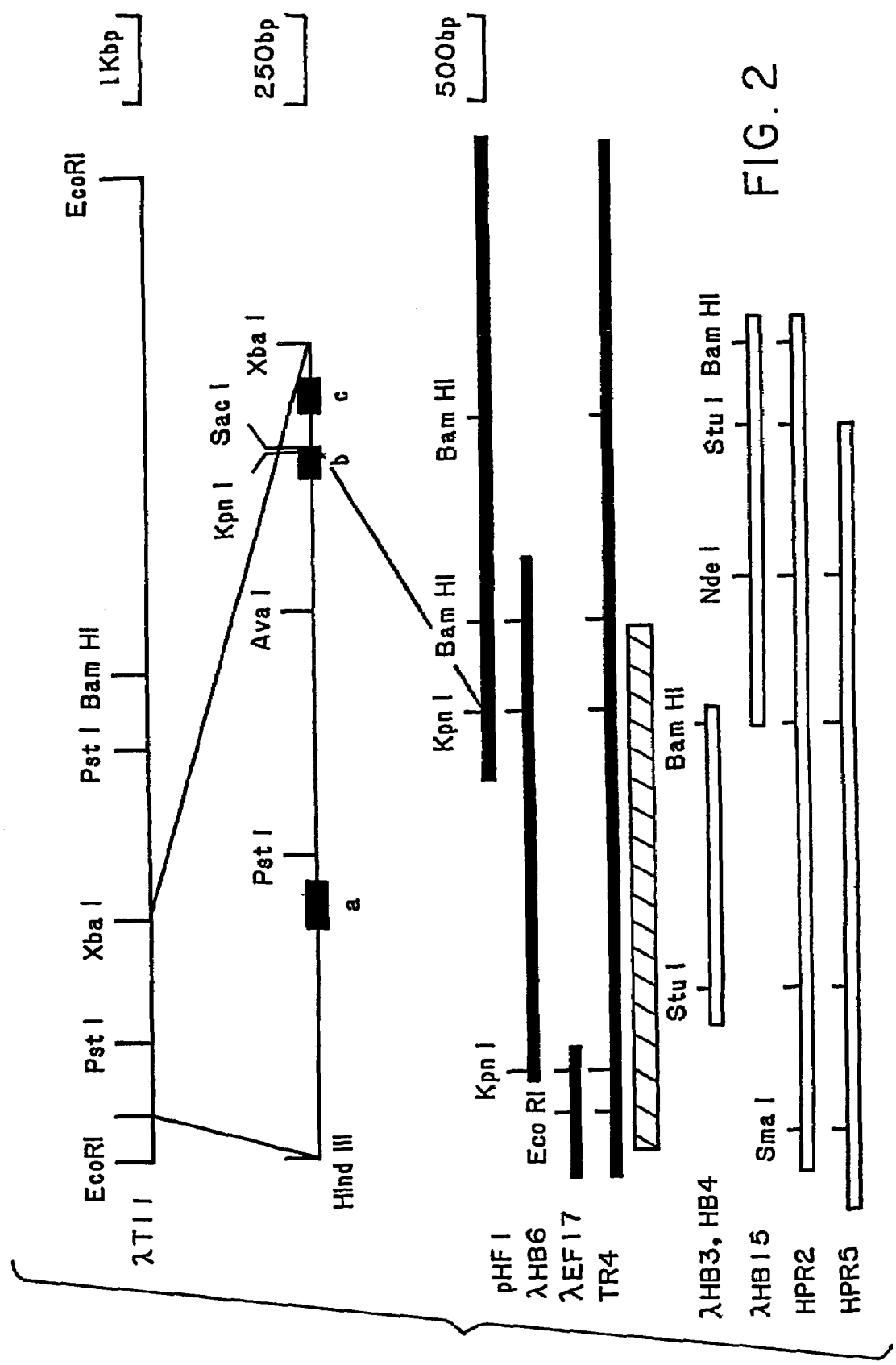
FIG. 2 Molecular cloning of the λT11 genomic fragment as well as cDNAs of T11 and PDGF-R genes. Restriction map of: λT11 genomic clone (solid lines); T11 cDNA clones (solid bars); and PDGF-R cDNA clones (open bars). Coding regions within three fragments, as determined by nucleotide sequencing analysis, are indicated by black boxes labeled a, b and c.

The restriction enzyme digestion maps of cDNA clones HF1, HB6, EF17 and TR4, and their mapping relationships to genomic clone T11, are displayed in FIG. 2. The sense strand DNA nucleotide sequence, and the predicted primary protein sequence encoded, are shown in FIG. 3 for the TR4 cDNA clone, the largest cDNA clone related to the T11 gene.

Figure 1A:
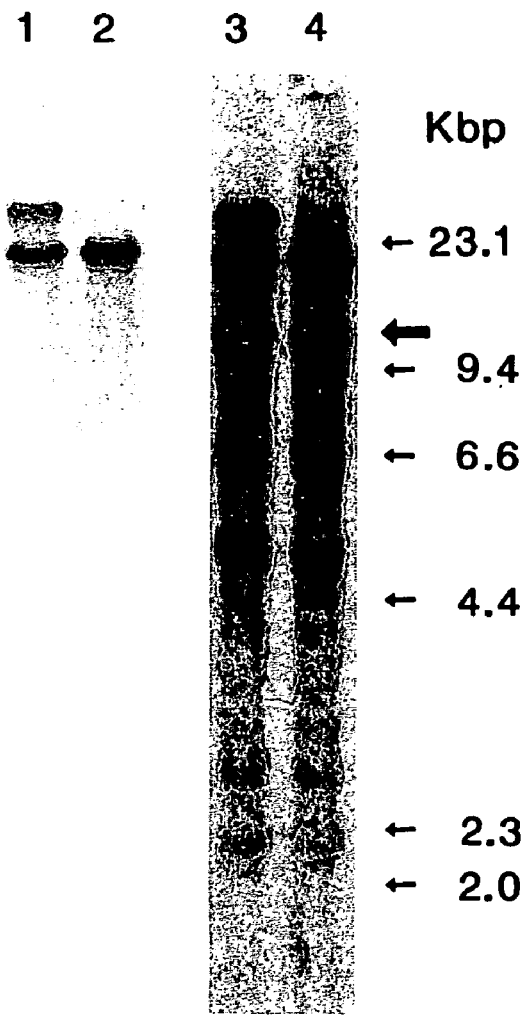
FIG. 1 Detection of v-fms and PDGF receptor related gene fragments in human placenta and thymus DNAs. Hybridization of a v-fms probe (A) or a mouse PDGF receptor probe (B) to human placenta (lane 1 and 3) or thymus (lane 2 and 4) DNAs under stringent (50% formamide; lane 1 and 2) or relaxed (30% formamide; lane 3 and 4) hybridization conditions. Arrows indicate the 12-kbp EcoRI fragment detected under relaxed conditions by both v-fms and mouse PDGF-R probes.
Figure 1B:
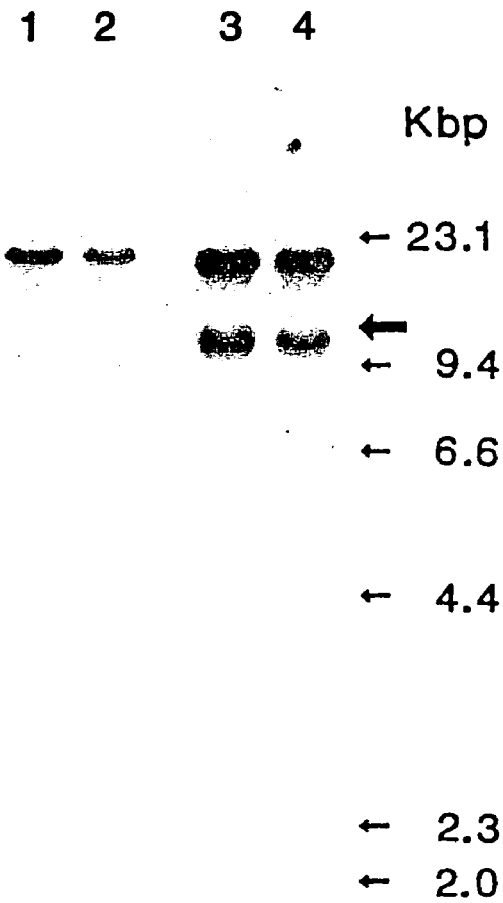

As described in the Experimental Section, the T11 genomic clone comprises a clone of genomic fragment of normal human thymus DNA containing a 12-kbp sequence bounded by recognition sites for the restriction enzyme EcoRI, which fragment hybridized more strongly in analyses by blot hybridization than other fragments with DNA probes derived from the tyrosine-kinase domains of both the viral oncogene v-fms and the mouse cellular PDGF-R gene (see FIG. 1). The T11 genomic clone contains most of the blocks of sequences found in the mRNA product of the T11 gene (i.e., the exons), in addition to intervening gene sequences not found in the mRNA (i.e., introns).

Other DNAs of this invention include the recombinant molecules comprising T11-related genomic or cDNA clones of this invention and any of the following vector DNAs: a bacteriophage λ cloning vector (exemplified by λEMBL4 or λgt11); or a mammalian expression vector (such as the pSV2 gpt vector into which the simian sarcoma virus promoter was engineered) capable of expressing inserted DNAs in mammalian (e.g., COS-1) cells.

Genomic clone T11 DNA was isolated, by standard gene cloning methods well known in the art, from a genomic library constructed from EcoRI-digested normal human thymus DNA which was size-selected by sucrose gradients and cloned into the λEMBL-4 vector system. The λT11 clone was identified on the basis of hybridization with both v-fms and mouse PDGF-R probes only under relaxed but not stringent hybridization conditions. Further details of the cloning strategy and probes are provided below and in the following Experimental Section.

A plasmid containing the HF1 cDNA clone, designated pHF1, was isolated by standard, well known methods, from a normal human fibroblast cDNA library in the Okayama-Berg expression vector under stringent conditions using the 0.9-kbp HindIII-PstI fragment of T11 which is a most preferred DNA of this invention. It contains a 3.9-kbp cDNA insert which hybridized to a 6.4-kb RNA transcript in normal human fibroblasts and contains a polyadenylation signal followed by a poly(A) tail at its 3' end. It also contains the coding sequence within the λT11 DNA and 170 nucleotides related to CSF1-R and PDGF-R tyrosine kinase domains upstream of exon (a).

The cDNA clone kHB6 was isolated by standard methods using the 0.4-kbp 5' end of clone HF1 to screen a human infant brain cDNA library in the λgt11 vector.

Another cDNA clone, λEF17, isolated by screening a human embryo fibroblast (M426 cell line) cDNA library, prepared by random priming of DNA synthesis on mRNA template and cloning in the λgt11 vector, with a 0.2-kbp 5' fragment of λHB6 as a probe. A possible ATG initiation codon was identified within EF17.

The three overlapping clones (pHF1, λHB6 and λEF17) contain the entire coding region in addition to 138-bp 5' and 3-kbp of 3' untranslated sequences (FIG. 2).

Figure 4:
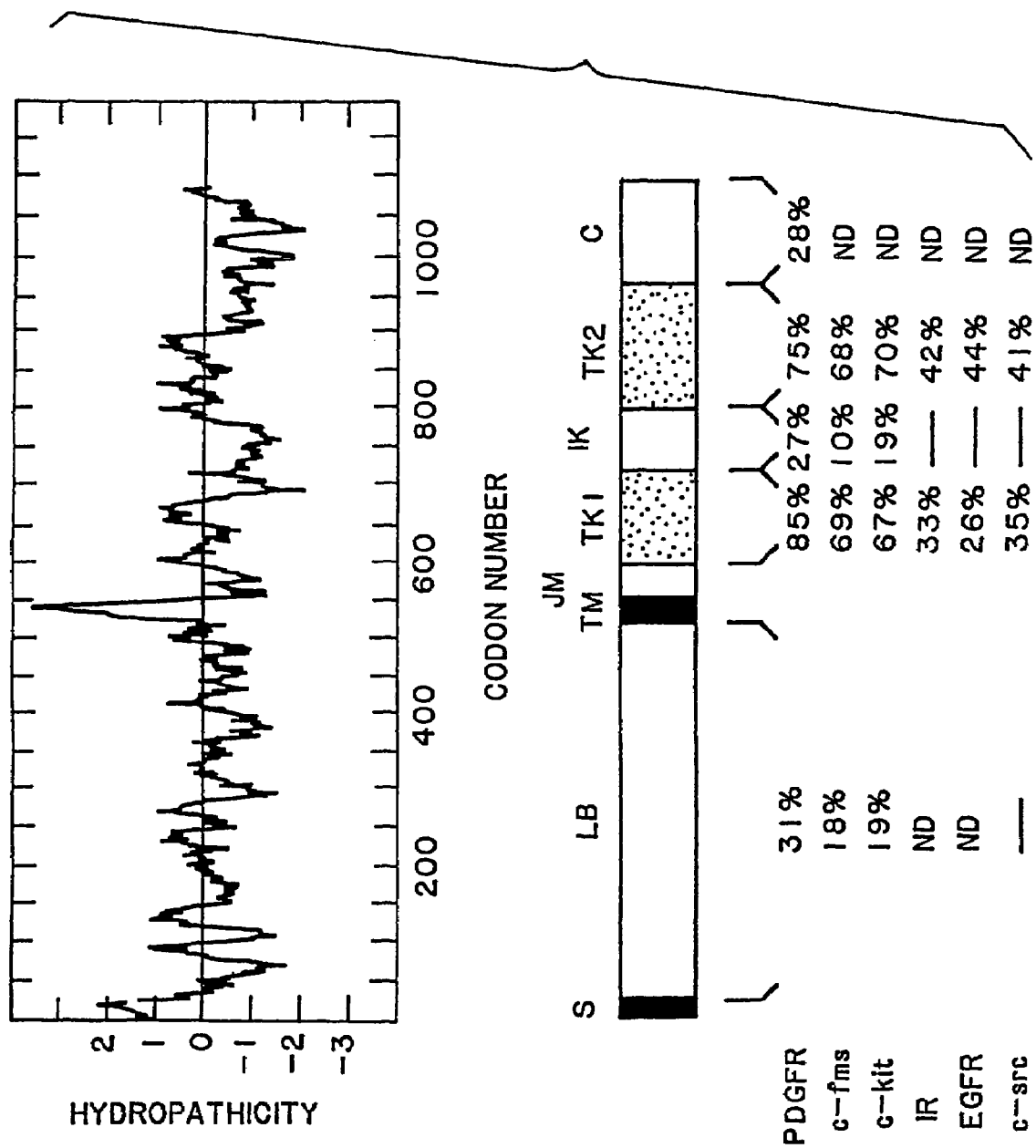
FIG. 4 Hydropathicity profile and homology with other tyrosine kinases of the T11 receptor like gene product. A schematic diagram of the predicted protein domains shows the signal sequence (S; black box), ligand binding domain (LB), transmembrane domain (TM; second black box), juxtamembrane domain (JM), tyrosine kinase domains (TK1, TK2; hatched boxes), inter-kinase domain (IK) and carboxyl terminus (C). The hydropathicity profile was calculated by the method of Kyte and Doolittle (46). The homology percentages shown refer to identical amino acids within each respective domain. Abbreviations: IR, insulin receptor; EGF-R, epidermal growth factor receptor; ND, not determined.

The cDNA clone TR4 was obtained using a 5' 0.2-kbp subfragment of λEF17 to screen a M426 human embryo fibroblast cDNA library in a "phagemid" (phage and plasmid hybrid) vector (10). The 6.4-kbp TR4 cDNA clone includes an open reading frame beginning with a possible ATG initiation codon at nucleotide position 139 and extended to a TAA termination codon at position 3406 (see FIG. 3). Moreover, the first 23 amino acid stretch displayed properties of a cleavable hydrophobic signal peptide (FIGS. 3 & 4). The open reading frame was followed by 3-kbp of untranslated sequences and a polyadenylation signal (AATAAA) located 25 nucleotides upstream from the poly(A) sequence at the 3' end of the cDNA.

cDNA expression plasmids were constructed using standard cloning methods well known in the art, by introducing the T11-related cDNA encompassing nucleotides 1 to 3454 (FIG. 3) into the pSV2 gpt vector into which the simian sarcoma virus long-terminal—repeat (LTR) had been engineered as the promoter, as previously described in detail (49).

DNAs and sense strand RNAs of this invention can be employed, in conjunction with protein production methods known in the art, to produce cells expressing functional type α PDGF-R protein from the novel gene in the absence of other PDGF receptors. These novel receptors can be used for functional studies in cells, such as qualitative and quantitative receptor binding assays.

Figure 7A:
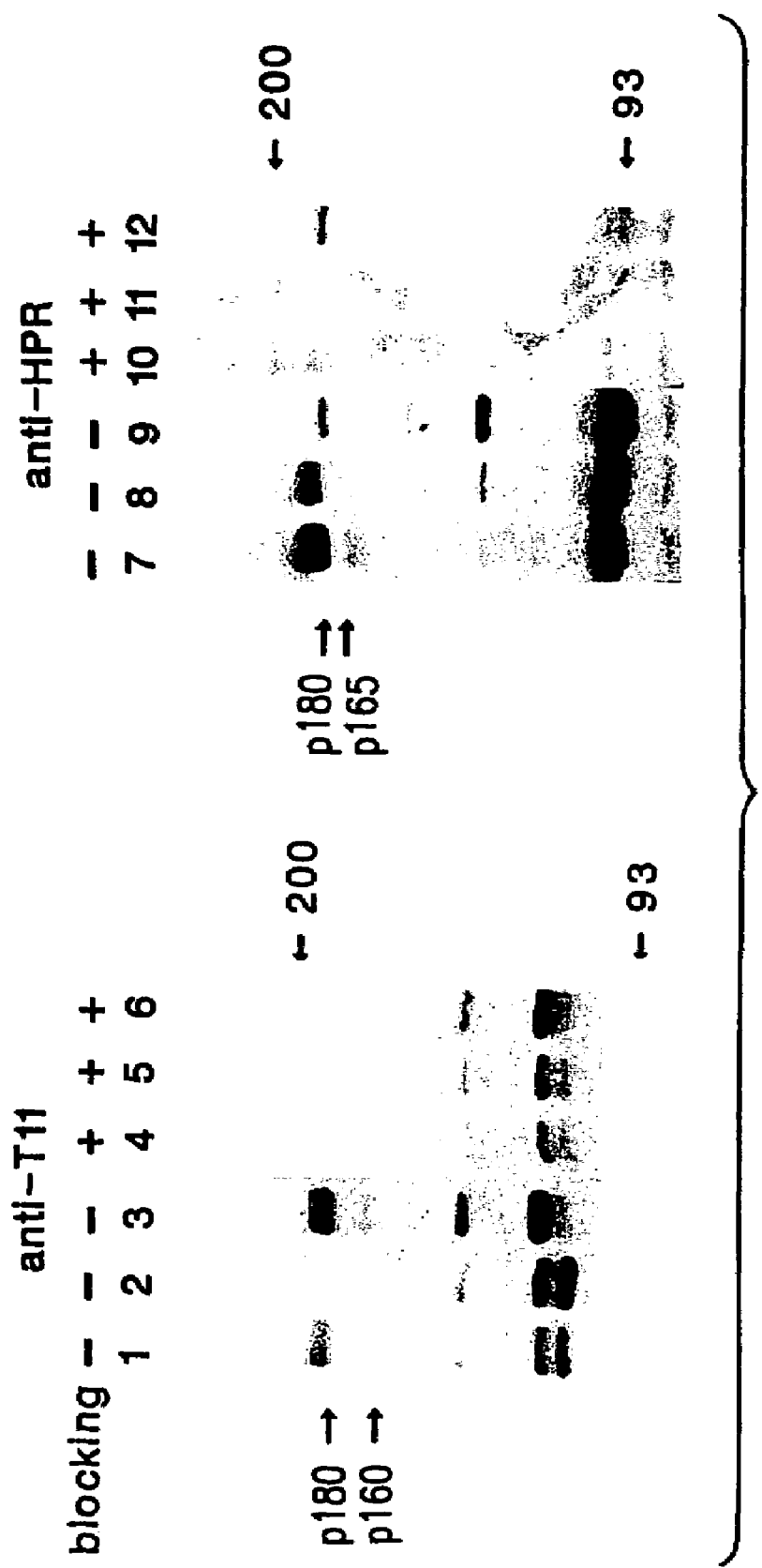
FIG. 7 Detection of T11 and PDGF-R proteins with peptide antisera in human cell lines (A) and COS-1 cell transfectants (B). (A) M426 human embryo fibroblasts (lanes 1, 4,7 and 10), 8387 fibrosarcoma cells (lanes 2, 5, 8 and 11), A204 rhabdomyosarcoma cells (lanes 3, 6, 9 and 12), (B) COS-1 cells (lanes 1 and 4), COS-1 cells transfected with vectors carrying T11 cDNA (lanes 2 and 3) or PDGF-R cDNA (lanes 5 and 6).
Figure 7B:
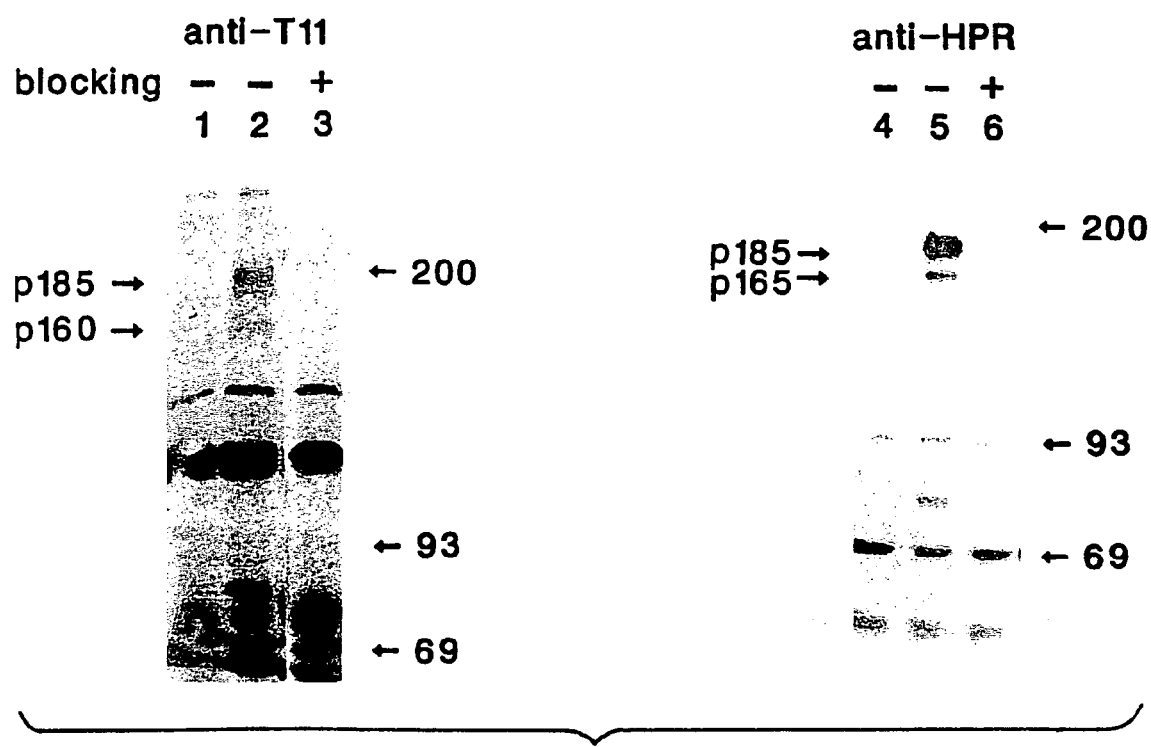

Accordingly, one embodiment of this aspect of this invention comprises a cell, preferably a mammalian cell, transformed with a DNA of the invention, wherein the transforming DNA is capable of being expressed. Mammalian cells (COS-1) transformed with the pSV2 gpt vector carrying a T11-related cDNA were prepared according to well-known methods and were shown to express T11 gene products as 185 kd and 160 kd species (FIG. 7B). These products were capable of binding human PDGF isolated from platelet, as illustrated in the Experimental Section below (see, FIG. 8).

Additional work in the Experimental Section demonstrates further that DNAs of this invention can be used to reconstitute type α PDGF receptor gene function in other cells free of PDGF receptors, and that each receptor type, α or β, efficiently mediates major known PDGF activities including mitogenic signal transduction, chemotaxis and stimulation of phosphoinositide turnover. Moreover, these studies further establish the type α PDGF receptor as the principal receptor for the main form of human PDGF which is derived from platelets.

Thus, by so using the DNAs of the invention in gene expression methods, especially the preferred TR4 cDNA clone listed herein, those skilled in the art, without undue experimentation, can construct cell systems which fall within the scope of this invention, for determining the mechanisms of PDGF regulatory processes, as well as for production of large amounts of the novel PDGF receptor protein.

This invention further comprises novel bioassay methods for detecting the expression of genes related to DNAs of the invention. According to one such embodiment, DNAs of this invention may be used as probes to determine levels of related mRNAs. This embodiment is exemplified by the comparison of mRNA species of the T11 and known PDGF-R genes in normal and tumor cells (FIG. 6). Total or polyadenylated RNA was separated by denaturing gel electrophoresis in formaldehyde (48), transferred to nitrocellulose, and hybridized under stringent conditions with $^{32}$P-labeled probes. The probes were prepared from any of the following DNAs of this invention: clone pT11-HP (0.95-kbp HindIII-PstI fragment of genomic clone T11) or from T11 cDNA (3.5-kbp BamHI fragment of TR4, including the whole coding region).

Therefore, by employing the DNAs and RNAs of the invention in known hybridization methods, especially the most preferred DNAs listed herein, those skilled in the art, without undue experimentation, can measure levels of expression of type α PDGF-R gene without interference from mRNA of type β PDGF-R gene or other related oncogenes.

This invention also comprises novel antibodies made against a peptide encoded by a DNA segment of the invention or by other related DNAs. This embodiment of the invention is exemplified by rabbit antisera containing antibodies which specifically bind to type α PDGF-R protein or, in the alternative, to the known PDGF-R protein, herein designated type β.

Such type specific antisera were raised to synthetic peptides representing 15 amino acid sequences from the carboxyl-terminal regions of their respective PDGF-R proteins (residues 959-973 of the type α sequence displayed in FIG. 3, and corresponding residues 967-981 of the known type β sequence, as predicted by the respective cDNA sequences). These peptides were selected to meet the following criteria: lack of sequence relatedness between the two PDGF-R types (less than 50% sequence homology); relative hydrophilicity; and carboxyl-terminal location which is known to be associated with a higher likelihood of producing antibodies reactive with native proteins.

Antisera to peptides were prepared by chemically synthesizing the peptides, conjugating them to carrier (thyroglobulin), and injecting the conjugated peptides into rabbits with complete Freund's adjuvant, according to standard methods of peptide immunization.

These antibodies can be used for detection or purification of the protein products. Thus, FIG. 7 shows the use in Western blot experiments of two different rabbit antibodies (anti-T11 (PDGF-R type α) and anti-HPR (PDGF-R type β)] raised against the corresponding type-specific peptides. As is evident from th figure, the appropriate PDGF-R types are specifically detected in various cells by antisera from rabbits immunized with synthetic peptides.

Experimental Section

This section describes experimental work leading to the identification and cloning of a genomic sequence and cDNAs of a novel receptor-like gene of the PDGF receptor/CSF-1 receptor subfamily. The gene gives rise to a 6.4-kb RNA transcript that is coexpressed in normal human tissues with the known 5.3-kb PDGF receptor mRNA. The new PDGF receptor gene was localized to chromosome 4 at location 4q 11-12, consistent with the clustering of other genes of this receptor subfamily on ancestrally related chromosomes 4 and 5.

That the cloned cDNA is functional is demonstrated by the observation that introduction (by transfection using a viral vector) of a cDNA of the novel gene into COS-1 cells leads to expression of proteins which are specifically detected with anti-serum directed against a predicted peptide. Transfected but not control COS-1 cells demonstrate specific binding of $^{125}$I-human PDGF, which is efficiently competed by all three PDGF isoforms, including the main AB form found in human platelets. In contrast, expression of the known PDGF receptor cDNA in COS-1 cells leads to PDGF binding with a distinct pattern of competition by the same PDGF isoforms characterized by a marked preference for PDGF form BB.

Further evidence that the new receptor gene encodes a distinct PDGF receptor derives from examination of human cells, originally free of PDGF receptors, in which PDGF-receptor activities are reconstituted by either type α or type β receptors introduced by transfection with vectors bearing the respective cDNAs. Cells with the type α receptors are significantly more responsive to PDGF-AB in all of the following PDGF-mediated cellular activities: tyrosine phosphorylation of the receptor gene product; stimulation of DNA synthesis and consequent cell proliferation; chemotaxis; phosphoinositide breakdown; and cytosolic calcium mobilization ([$Ca^2+$]i).

Thus, while each type of reconstituted PDGF-R gene product independently elicits similar biochemical as well as biological responses to PDGF-BB, the type α PDGF-R is the preferred receptor for PDGF-AB, the principal isoform of human PDGF which is found in platelets. Accordingly, it follows that abnormalities in the structure or expression of the type α PDGF receptor could have profound pathological effects for which the present invention provides means of diagnosis and therapy.

Materials and Methods

Detection of v-fms and 2DGF receptor-related gene fragments in-human placenta and thymus DNAs. Genomic DNA (20 μg) was digested with EcoRI, separated by electrophoresis in 0.8% agarose gels, and transferred to nitrocellulose paper (41). Hybridization to $^{32}$P-labeled probes (42) was conducted in a solution of 50% or 30% formamide, 0.75 M NaCl, and 0.075 M sodium citrate, at 42° C. (43). After hybridization, the blots were washed in 2×SSC (0.3 M NaCl; 0.03 M sodium citrate) at room temperature, and then in 0.1× or 0.6×SSC at 50° C. (stringent or relaxed condition, respectively). The v-fms probe was a 0.44-kbp XhoI-BglI fragment encompassing nucleotides 3891 to 4419 of the v-fms oncogene (44). The mouse PDGF receptor probe was a 0.5-kbp SinI-PvuI fragment encompassing nucleotide 2490 to 2995 of its cDNA (6).

Molecular cloning of the 8T11 genomic fragment as well as cDNAs of T11 and PDGF-R genes. Libraries from which specific cDNA clones (in parentheses) were isolated included: human fibroblast mRNAs in the Okayama-Berg vector (pHF); human infant brain mRNAs in λgt11 (λαHB) human embryonic fibroblast random primed mRNAs in λgt11 (λEF); and human embryonic fibroblast mkNAs in the directional cloning phagemid (TR4 or HPR) Restriction sites were determined by electrophoretic analysis of the products of single and double digestions. Regions of λT11 homologous to the v-fms or mouse PDGF receptor probes were identified by hybridization as described in FIG. 1. Three restriction fragments (0.95-kbp HindIII-PstI 0.5-kbp AvaI-SacI, and 0.35-kbp KpnI-XbaI) including regions homologous to the v-fms and mouse PDGF receptor probes were subcloned into plasmids and sequenced by the dideoxy chain termination method (45).

Chromosome mapping of the T11 gene. The probe was labeled with all four $^3$H-nucleotides (New England Nuclear, Boston, Mass.) using a modified nick translation kit (Amersham, Arlington Heights, Ill.) to a specific activity of 2.5× $10^7$ cpm/μg DNA. In situ hybridization with human metaphases and prometaphases from methotrexate-synchronized peripheral lymphocyte cultures was carried out as previously described (47).

Comparison of mRNA-species by Northern blot hybridization. Total or polyadenylated RNA was separated by denaturing gel electrophoresis in formaldehyde (48), transferred to nitrocellulose, and hybridized under stringent conditions (50% formamide, 0.075M NaCl, 0.75M sodium citrate, at 42° C.) with $^{32}$P-labeled probes.

Detection of T11 and PDGF-R proteins with peptide antisera. Anti-T11 and anti-PDGF-R sera were obtained following immunization of rabbits with 15 amino acid peptides from the corresponding carboxyl-terminal regions of the predicted receptors. These peptide sequences were less than 50% homologous. cDNA expression plasmids were constructed by introducing the T11 cDNA encompassing nucleotides 1 to 3454 (FIG. 3) or the PDGF-R cDNA encompassing nucleotides I to 3939 into the pSV2 gpt vector into which the simian sarcoma virus LTR had been engineered as the promoter (49). About $10^6$ COS-1 cells in 10 cm petri dishes were incubated in Dulbecco's modified Eagle's medium (DMEM) supplemented with 10% fetal calf serum 24 hr prior to transfection. DNA transfection was performed by the calcium phosphate precipitation method (50) 48 hours prior to analysis. Cultures were lysed with staph-A buffer (10 mM sodium phosphate pH7.5, 100 mM NaCl, 1% Triton X-100, 0.1% SDS, 0.5% deoxycholate, 0.1% aprotinin, 1 mM PMSF, and 1 mM sodium orthovanadate) and clarified by centrifugation at 10,000×g for 30 min. Proteins (100 φg per lane) were resolved by electrophoresis in 7% SDS-polyacrylamide gels, transferred to nitrocellulose filters and probed by immunoblot analysis (with or without peptide blocking) using $^{125}$I-Protein A (51).

Binding of $^{125}$I-labeled human PDGF to receptors on cells. COS-1 cells were plated in 12-well plates and transfected 48 hours before assay as described in FIG. 7. Human PDGF was labeled with $^{125}$I by the chloramine-T method to specific activities of 3.7×$10^4$ cpm/ng (52). The binding of $^{125}$I-labeled PDGF isolated from human platelets (53) in the absence or presence of a 50-100 fold excess of unlabeled human PDGF (AB) (Collaborative Research), recombinant PDGF-BB (AmGen) or recombinant PDGF-AA (37), was carried out at 4° C. for 2 hrs. Unbound $^{125}$I-PDGF was removed by four successive washes with binding buffer (DMEM containing 1 mg per ml bovine serum albumin). The cells were then lysed in solubilizing buffer (1% Triton X-100, 20 mM Hepes pH 7.4, 10% [v/v] glycerol), and radioactivity measured with a T counter.

Tyrosine autophosphorylation of type α and type β-PDGF-R gene products. After incubation with PDGF for 5 min at 37° C., cell lysates were immunoprecipitated with anti-peptide antisera. Total cell lysates or immunoprecipitates were analyzed by immunoblotting with antibodies to the receptors or to phosphotyrosine (anti-P-Tyr) (54). The anti-phosphotyrosine antibodies were preincubated with 10 mM phosphotyrosine for blocking.

Results

Detection of a novel human PDGF-R/CSF1-R-related gene. In order to explore novel sequences related to known growth factor receptor genes of the PDGF-R/CSF1-R family, high molecular weight DNAs prepared from human placenta and thymus were digested with EcoRI and analyzed by blot hybridization with DNA probes derived from the tyrosine-kinase domains of v-fms and the mouse PDGF-R gene (FIG. 1). Under stringent conditions, the v-fms probe detected EcoRI restriction fragments of 27-kbp and/or 20-kbp, due to the previously reported restriction polymorphism at this locus (8). Under less stringent conditions, several additional fragments of 12-, 6.8-, 5-, 2.7-, 2.2-kbp, which hybridized to the v-fms probe, were observed. The corresponding region of the mouse PDGF-R cDNA hybridized with a single 21-kbp fragment under stringent conditions (FIG. 1).

At lower stringency, the same probe detected several additional fragments, some of which had sizes similar to those of the v-fms-related fragments described above. Among these, the 12-kbp EcoRI fragment hybridized more strongly than the other fragments with both probes. Moreover, some of the smaller bands corresponded to restriction fragments reported for human c-kit (7). Thus, it was decided to clone the 12-kbp EcoRI DNA fragment and characterize it more fully.

Using the XEMBL-4 vector system, a genomic library size-selected by sucrose gradients was constructed from EcoRI-digested normal human thymus DNA. FIG. 2 shows the restriction map of λT21 containing a 12-kbp EcoRI insert, which hybridized with both v-fms and mouse PDGF-R probes only under relaxed but not stringent hybridization conditions. Regions homologous to v-fms/PDGF-R tyrosine kinase domains were localized by hybridization to restriction endonuclease digests of λT11 DNA.

Three plasmid subclones containing sequences hybridizing to the 0.95-kbp HindIII-PstI 0.5-kbp AvaI-SacI, and 0.35-kbp KpnI-XbaI fragments of λT11 were subjected to nucleotide sequence analysis. Their discrete open reading frames (FIG. 3) showed relatedness to both human c-fms and mouse PDGF-R genes, but were readily distinguished from each of these genes (3,6) as well as from c-kit (7). The three putative coding regions were each flanked by the AG and GT dinucleotides that border the exons of eukaryotic genes (9).

To assess whether the T11 sequence was transcribed, Northern blot analyses of a variety of cells were performed using a clone of the 0.95-kbp HindIII-PstI fragment (pT11-HP) which contained exon (a) (FIG. 2) and lacked human repetitive sequences. Under stringent conditions, a single 6.4-kb RNA transcript was detected in poly(A)+ RNA prepared from normal human fibroblasts (data not shown). This transcript differed in size from previously reported transcripts for the PDGF-R (6), c-fms (3) or c-kit genes (7). All of these findings indicated that the T11 sequence represented a gene distinct from known members of this subfamily of tyrosine kinase receptors.

cDNA cloning of the novel gene. A normal human fibroblast cDNA library in the Okayama-Berg expression vector was initially screened under stringent conditions using the pT11-HP clone of the 0.9-kbp HindIII-PstI fragment of λT11. One strongly hybridizing clone containing a 3.9-kbp cDNA insert was isolated (FIG. 2). This clone, designated pHF1, hybridized to a 6.4-kb transcript in normal human fibroblasts and contained a polyadenylation signal followed by a poly(A) tail at its 3' end. It also contained the coding sequence within the λT11 DNA and 170 nucleotides related to CSF1-R-PDGF-R tyrosine kinase domains upstream of exon (a).

The 0.4-kbp 5' end of pHF1 was used to search for overlapping cDNA clones in a human infant brain library. Under stringent conditions, a number of positive clones with similar restriction maps were isolated (data not shown). The longest, λHB6, (FIG. 2) was subjected to sequence analysis. A possible ATG initiation codon was identified within another clone, kEF17, isolated by screening a M426 human embryo fibroblast cDNA library in the λgt11 vector with a 0.2-kbp 5' fragment of λHB6 as a probe. The three overlapping clones (pHF1, λHB6 and λEF17) contained the entire coding region in addition to 138-bp 5' and ~3-kbp of 3' untranslated sequences (FIG. 2).

Two clones, λHB3 and λHB4, that gave weaker signals in plaque hybridization during screening of the human infant brain library were also sequenced. These showed close similarity to the sequence of the mouse PDGF-R cDNA (6). Moreover, when the 2.0-kbp insert of HB4 was hybridized to normal human fibroblast RNA, it detected a transcript of 5.3-kb, consistent with that of the PDGF-R (6).

No clones containing sequences further upstream from the 5' end of λHB4 could be obtained by screening the human infant brain cDNA library in λgt11. This was accomplished by utilizing a M426 human embryo fibroblast cDNA library in a new phagemid vector constructed as described elsewhere (10). By screening this library with a 0.3-kbp 5' subfragment of λHB3, two overlapping clones, HPR2 and HPR5, were obtained. These contained between them the entire known human PDGF-R coding sequence, its complete 3' untranslated region, and 360 nucleotides of its 5' untranslated region (FIG. 2). A 6.4-kbp cDNA clone (TR4) of the novel related gene was also obtained from this same library by screening with a 5' 0.2-kbp subfragment of λEF17.

Deduced amino acid sequence establishes the T11 gene as a member of the PDGF-R/CSF1-R subfamily. The complete nucleotide sequence of the 6.4-kbp cDNA of the T11 gene is shown in FIG. 3. An open reading frame beginning with a possible ATG initiation codon at nucleotide position 139 extended to a TAA termination codon at position 3406. Although the open reading frame extended further upstream, the putative initiation ATG was flanked by sequences that fulfill the Kozak criteria for an authentic initiation codon (11). Moreover, the first 23 amino acid stretch displayed properties of a cleavable hydrophobic signal peptide (FIGS. 3 & 4). At the 3' end, the open reading frame was followed by ~3-kbp of untranslated sequences. A polyadenylation signal (AATAAA) was located 25 nucleotides upstream from the poly(A) sequence at the 3' end of the cDNA.

According to the putative cleavage site for the signal peptide (12), the amino terminus of the mature product was predicted to be glutamine at amino acid 24 followed by 1066 amino acids. This polypeptide sequence with a calculated molecular mass of around 120 kd contained all of the characteristics of a membrane-spanning tyrosine kinase receptor. A hydrophobic segment consisting of 24 amino acids (residues 525 to 548) exhibited characteristics of a receptor transmembrane domain (FIGS. 3 & 4). Between the signal peptide and the transmembrane domain, there was structural homology with the extracellular ligand binding domains of the PDGF-R/CSF1-R subfamily. Ten cysteine residues were spaced at the same positions as in the other receptors of this subfamily, and eight potential N-linked glycosylation sites were distributed in its putative extracellular domain (FIG. 3).

The cytoplasmic domain was comprised of a conserved tyrosine kinase region and a hydrophilic carboxyl-terminal tail (FIGS. 3 & 4). The tyrosine kinase domain included the consensus ATP binding sequence (residues Gly-X-Gly-X-X-Gly . . . Lys) and a tyrosine residue at position 849 homologous to the major autophosphorylation site of $pp60^{v\text{-}src}$ at position 416 (13). Moreover, the tyrosine kinase was divided into two domains by a hydrophilic inter-kinase sequence as previously shown for c-fms/CSF1-R, PDGF-R, and c-kit (FIG. 4).

The amino acid homologies of its extracellular domain with those of the PDGF-R, CSF1-R, and c-kit were 31%, 18%, and 19% respectively. The two kinase domains of the T11 gene were most homologous to those of the human PDGF receptor (85% and 75%, respectively) as compared with 67 to 70% for c-fms and c-kit (FIG. 4). Even in the inter-kinase domain, its amino acid sequence was more closely aligned to the PDGF-R with 27% homology compared to 10 and 19% with c-fms or c-kit. These observations lead to the conclusion that the T11 product was in the PDGF-R/CSF1-R subfamily and most closely related to the PDGF-R.

The deduced amino acid sequence of another cDNA clone (obtained in the same experiment which produced the TR4 cDNA clone) established its product as the known human PDGF receptor. Its sequence corresponded almost completely with the recently published sequence of the known human PDGF receptor (14). A single nucleotide difference changed residue 240 from Asn to Ser. Comparison with the mouse PDGF receptor cDNA amino acid sequence also revealed high similarities throughout all functional domains including the ligand binding domain (79%), transmembrane domain (96%), the juxtamembrane domain (97%), split tyrosine kinase domains (TK1, 99% and TK2, 97%), inter-kinase domain (86%) and carboxyl terminus (85%).

Figure 5A:
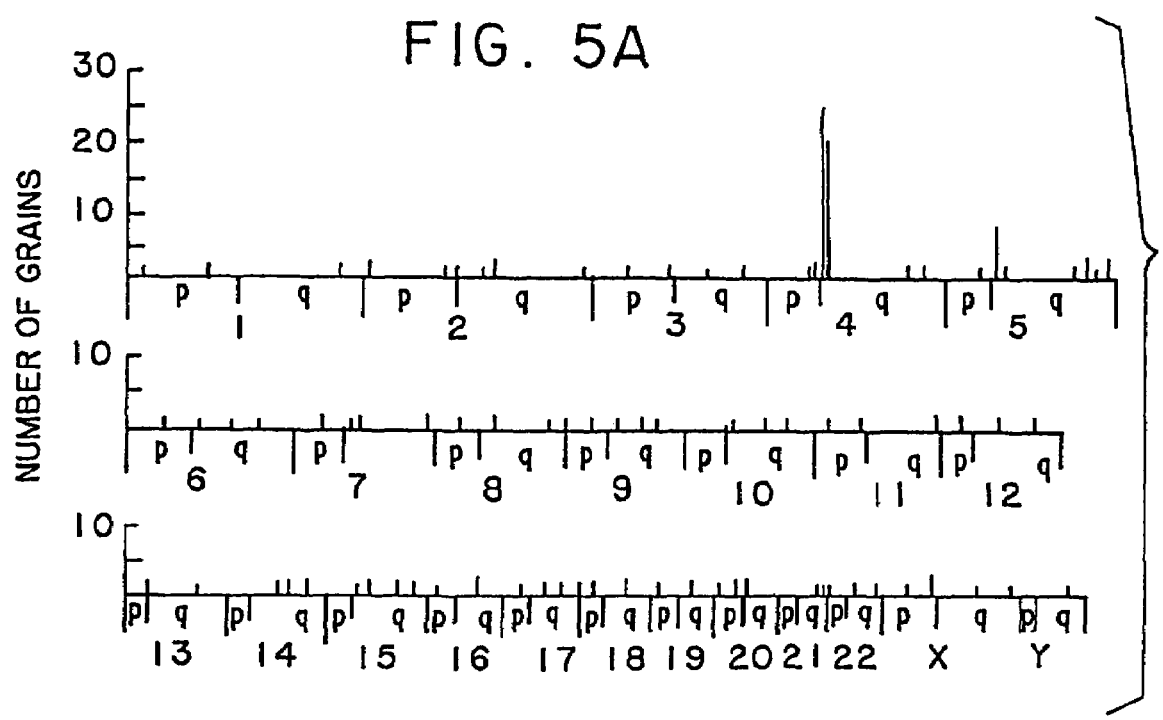
FIG. 5 Chromosome mapping of the T11 gene.
Figure 5B:
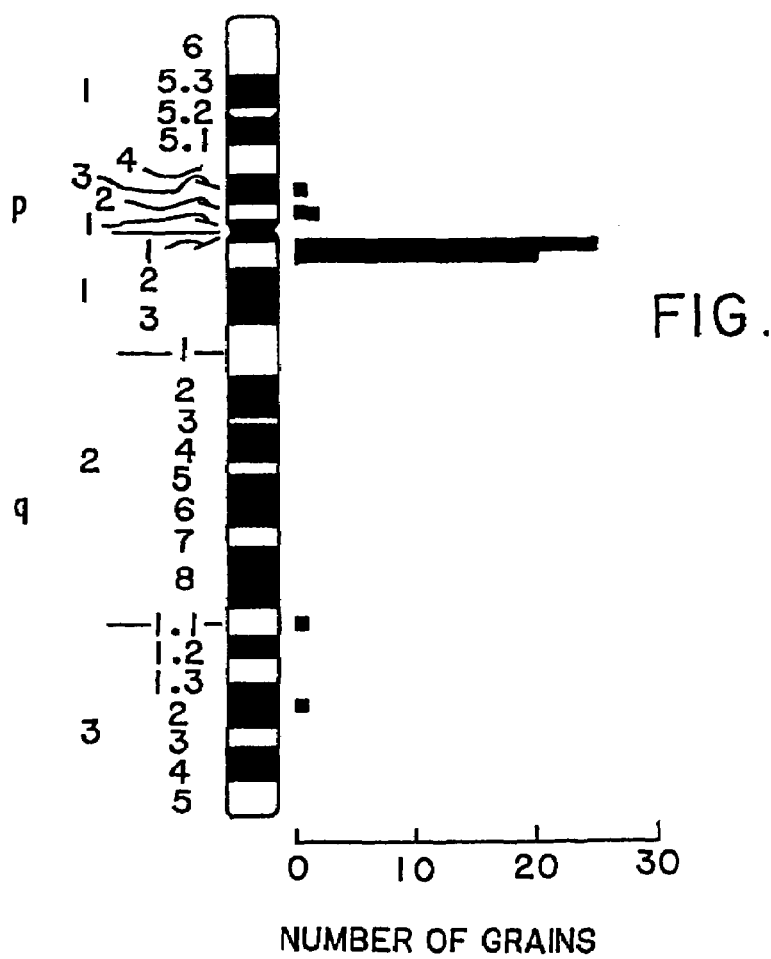

Chromosomal mapping of the T11 gene. To define the new gene with respect to chromosomal location, 104 chromosome spreads were examined by in situ hybridization with a pT11-P probe. A total of 136 grains were localized on a 400-band ideogram (FIG. 5). Of the total grains, 50 (37%) were on chromosome 4 with the majority of 45 grains tightly clustered near the acentromeric region of the long arm at bands, q11-12 (FIG. 5). A second site of hybridization on chromosome 5q 11.1-11.2 consisting of 7 grains accounted for 5% of the total grains (FIG. 5).

The T11 gene probe was also hybridized to chromosomes derived from a Burkitt lymphoma cell line carrying a large abnormal marker chromosome originating from a translocation t1;5 (p22; q23) translocation. There was no detectable labeling of the rearranged chromosome 5 in over 300 spreads examined for the presence of grains at this chromosome. Thus, in situ hybridization assigned the T11 gene to chromosome 4 at location q11-12. This localization places the new gene within the same region as the c-kit proto-oncogene (15). The structurally related genes for platelet factor 4, (16), interferon τ-inducible factor; τIP-10, (17) and melanoma growth stimulatory activity (MGSA) (18) as well as genes for α-feto protein, albumin (19), HPAFP (20), and the gene for dentinogenesis imperfecta have been mapped at 4q 11-13 (21).

Expression of transcripts and protein products of the endogenous T11 gene in normal and tumor cells. To investigate the tissue specific expression of the new receptor-like gene, either of the most preferred DNAs of this invention, i.e., the HindIII-PstI. 0.95-kbp fragment of the T11 genomic clone, or cDNA insert of TR4, was used for Northern blot hybridization experiments. A single 6.4-kb transcript was detected in poly(A)-containing RNAs of a variety of human tissues and cell lines. As shown in FIG. 6, relatively high levels of the transcript were found in smooth muscle, heart, and human embryo, while human liver and spleen demonstrated undetectable or barely detectable transcripts under these conditions.

Using a probe for the known human PDGF receptor gene, it was noted that the T11 and 5.3-kb PDGF-R transcripts appeared to be coexpressed at similar respective levels in each of these same tissues. Human skeletal muscle, fetal brain, placenta as well as cultured fibroblasts and glial cells also expressed high levels of both transcripts (data not shown).

Thus, the new gene and the known PDGF-R gene appeared to be coordinately expressed in normal tissues examined and exhibited a very different pattern from that reported for either c-fms/CSF1-R or c-kit (3,7).

Figure 6C:
FIG. 6 Comparison of mRNA species of the T11 and known PDGF-R genes, in normal and tumor cells. The same filter was first hybridized with the probe from pT11-HP (0.95-kbp HindIII-PstI genomic fragment) (A) and then rehybridized with a PDGF-R cDNA probe (B). A different filter was first hybridized with T11 cDNA (3.5-kbp BamHI fragment of TR4 including the whole coding region) (C) and then rehybridized with PDGF-R cDNA (3.8-kbp NdeI fragment of HPR2) (D). A and B contained poly (A)+ RNAs (5: µg per lane) extracted from human smooth muscle (lane 1), heart (lane 2), liver (lane 3), spleen (lane 4) or embryo (lanes 5 and 6). C and D contained total RNA (20: µg per lane) extracted from G402 leiomyoblastoma cells (lane 1), SK-LMS-1 leiomyosarcoma cells (lane 2), A1186 or A204 rhabdomyosarcoma cells (lanes 3 and 4), 8387 fibrosarcoma cells (lane 5), astrocytoma tissues (lanes 6 and 7), A1690 astrocytoma cells (lane 8), A1207 or A172 glioblastoma cells (lanes 9 and 10) or A875 melanoma cells (lane 11). Migrations of 28S and 18S ribosomal RNA (markers) are as indicated.
Figure 6C:
Figure 6C:
Figure 6C:
Figure 6D:

Expression of the T11 and PDGF-R genes were also compared in human tumor cells. Here, their patterns of expression could be readily distinguished. Several tumor cell lines were found to contain one or the other transcript but not both (FIGS. 6C and D).

Antibodies specific for either the novel or known PDGF receptor protein. In an effort to identify the protein product of the new gene, antisera to peptides were prepared based on its predicted sequence. Analogous regions of the predicted sequence of the known PDGF-R were utilized to generate antisera as well. Initial efforts to detect specific expression of the T11 gene product utilized M426 embryo fibroblast cells, from which cDNAs of both receptors had been isolated. 8387 and A204 cell lines which specifically expressed the PDGF-R or T11 gene transcripts, respectively were analyzed as well (FIG. 7A).

Western blot analysis of M426 cells with antisera (anti-T11) directed against the T11 gene product revealed 180 kd and 160 kd protein species, which were specifically competed by the immunizingpeptide. The anti-PDGF-R peptide serum (designated anti-HPR) detected 180 and 165 kd proteins in the same cells. Western blot analysis of 8387 cells revealed 180 and 165 kd species, which were recognized by the anti-HPR, but not by anti-T11 serum. Conversely, A204 cells contained 180 and 160 kd species which were specifically detected by anti-T11, but not recognized by anti-HPR serum.

All of these findings indicated that these antibodies of this invention were specific for detection of the homologous receptor gene product and that T11 gene products were expressed in cells containing its transcript.

Expression of T11 cDNA in a mammalian vector system. As further test of the ability to immunologically detect the T11 gene product as well as to investigate the functional expression of its cDNA, LTR-based expression vectors were constructed for the T11 cDNA encompassing nucleotides 1 to 3454 (FIG. 3) and for the corresponding known PDGF-R cDNA as well.

Transient expression in COS-1 cells led to the specific detection of the T11 gene products as 185 kd and 160 kd species (FIG. 7B) whereas the PDGF-R appeared as 185 kd and 165 kd proteins. The respective lower MW forms of each receptor did not vary in size among the cells analyzed. However, some different sizes of the higher MW species were observed, which were likely due to cell specific differences in glycosylation.

PDGF binding to the T11 product establishes it as a new PDGF-R gene. Because of their structural and deduced amino acid sequence similarities as well as their coexpression by normal cell types known to respond to PDGF, to studies were performed to determine whether the T11 gene product exhibited any functional relationship to the known PDGF-R gene product. Thus, $^{125}$I-labeled human PDGF was incubated with control and transfected COS-1 cells in the presence or absence of unlabeled PDGF isoforms.

Figure 8:
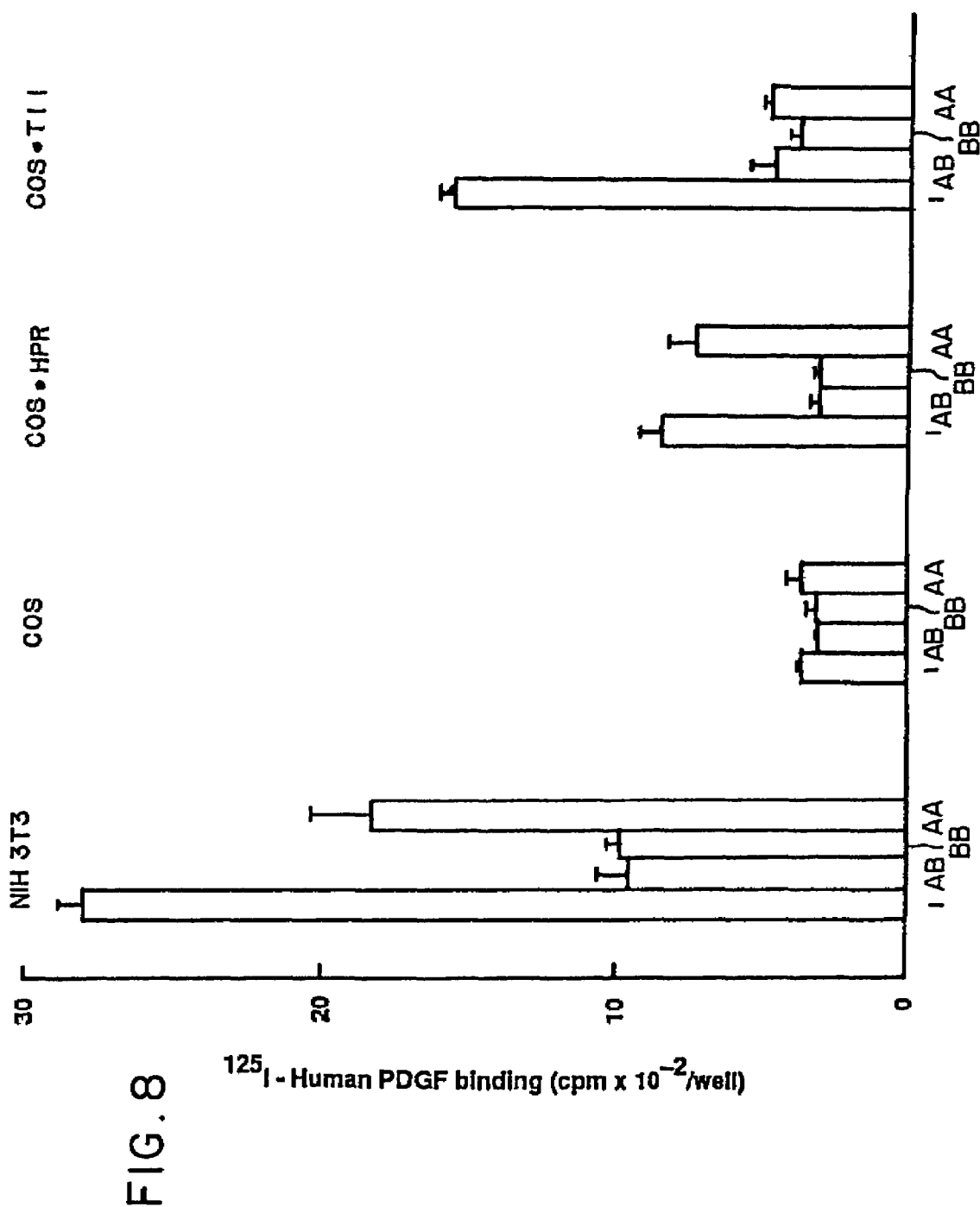
FIG. 8 Binding of $^{125}$I-labeled human PDGF to mouse control NIH/3T3, control COS-1 and COS-1 cells transfected with T11 or known PDGF-R cDNA expression vectors. Results represent the mean values (±SD), of triplicate samples.

As shown in FIG. 8, as much $^{125}$I-PDGF specifically bound to COS-1 cells transfected with the new receptor gene as to NIH/3T3 cells. Binding was reduced to the level of nontransfected COS-1 cells by competition with excess human PDGF (predominantly AB), PDGF-BB, or PDGF-AA. Specific binding of $^{125}$I-PDGF to COS-1 cells transfected with the PDGF-R cDNA was also observed. In this case, however, binding was competed by human PDGF (i.e., PDGF-AB) and PDGF-BB but not by PDGF-AA (FIG. 8).

Thus, while both T11 gene and PDGF-R gene products bound human PDGF, the pattern of competition by different PDGF isoforms distinguished the two receptors. These results implied that the T11 gene encoded a novel PDGF receptor with different affinities for the three dimeric forms of PDGF. Hence, the T11 receptor gene product was tentatively designated as the type α because PDGF binding was competed by AA as well as BB isoforms, and the product of the previously cloned PDGF receptor was designated as type β.

PDGF isoforms induce different patterns of autophosphorylation of the novel and known PDGF receptors. After PDGF binding to its receptor, a number of molecular events are rapidly triggered in vivo, including phosphorylation of the receptor protein on tyrosine residues (22). To compare the relative autophosphorylation of the products of the two PDGF-R genes by each PDGF isoform, the responses of A204 and 8387 cells that expressed type α and type β PDGF-R genes, respectively, were analyzed.

Figure 9A:
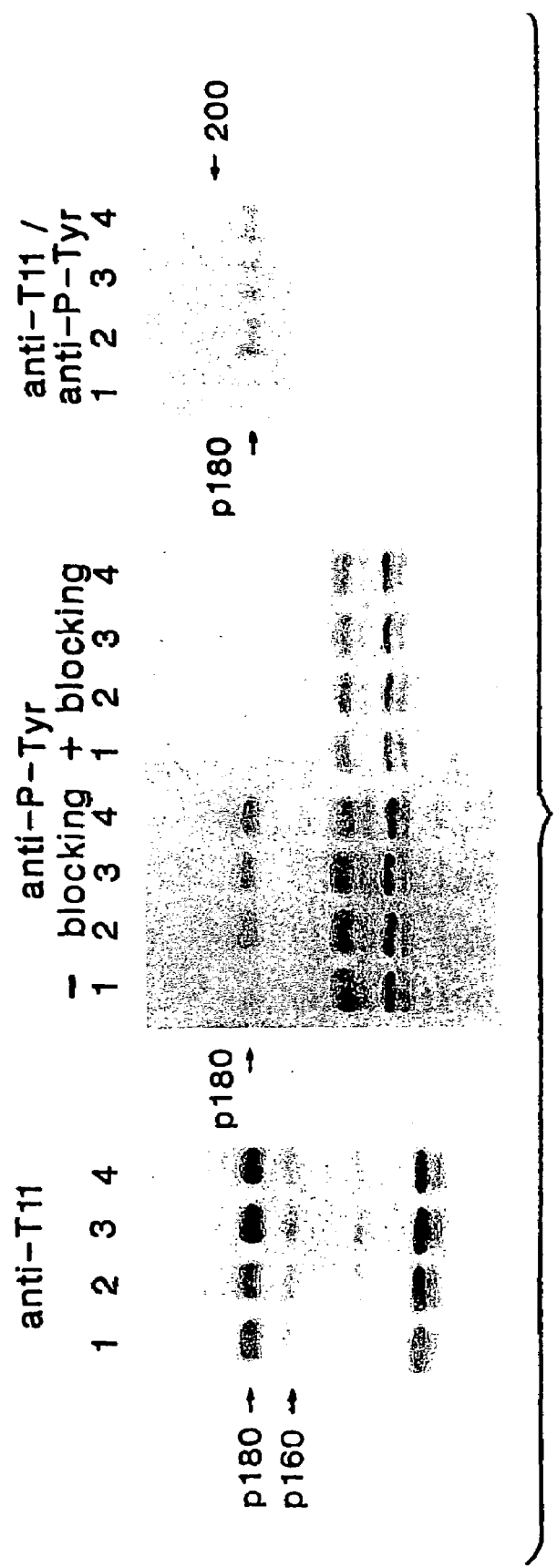
FIG. 9 Tyrosine autophosphorylation of type α and type β PDGF-R gene products induced by different PDGF isoforms. A204 (A), 8387 (B), or NIH/3T3 (C) cells were incubated with PDGF-BB (30 ng/ml) (lane 2), human PDGF (30 ng/ml) (lane 3), PDGF-AA (300 ng/ml) (lane 4) or 3 mM acetic acid (vehicle control: lane 1). Cell lysates were immunoprecipitated with peptide antisera directed against predicted type α or type β PDGF receptors (anti-T11 and anti-HPR, respectively). Immunoblot analyses was with antibodies to the receptors or phosphotyrosine (anti-P-Tyr) (54) as indicated above the blots. Arrows indicate the specific bands which were blocked in the presence of immunizing peptide.

As shown in FIG. 9A, immunoblots of A204 cells lysed 5 minutes following ligand exposure revealed readily detectable and very similar levels of autophosphorylation of a 180 kd species in response to each of the three PDGF isoforms. As further evidence that the induced autophosphorylation was specific to the type α receptor gene product, ligand stimulated A204 cell lysates were first subjected to immunoprecipitation with anti-type α PDGF-R serum (anti-T11) followed by immunoblotting with anti-phosphotyrosine serum. By this approach, it was firmly established that the 180 kd type α PDGF receptor was phosphorylated on its tyrosine with similar intensity in response to each of the three ligands.

Figure 9B:
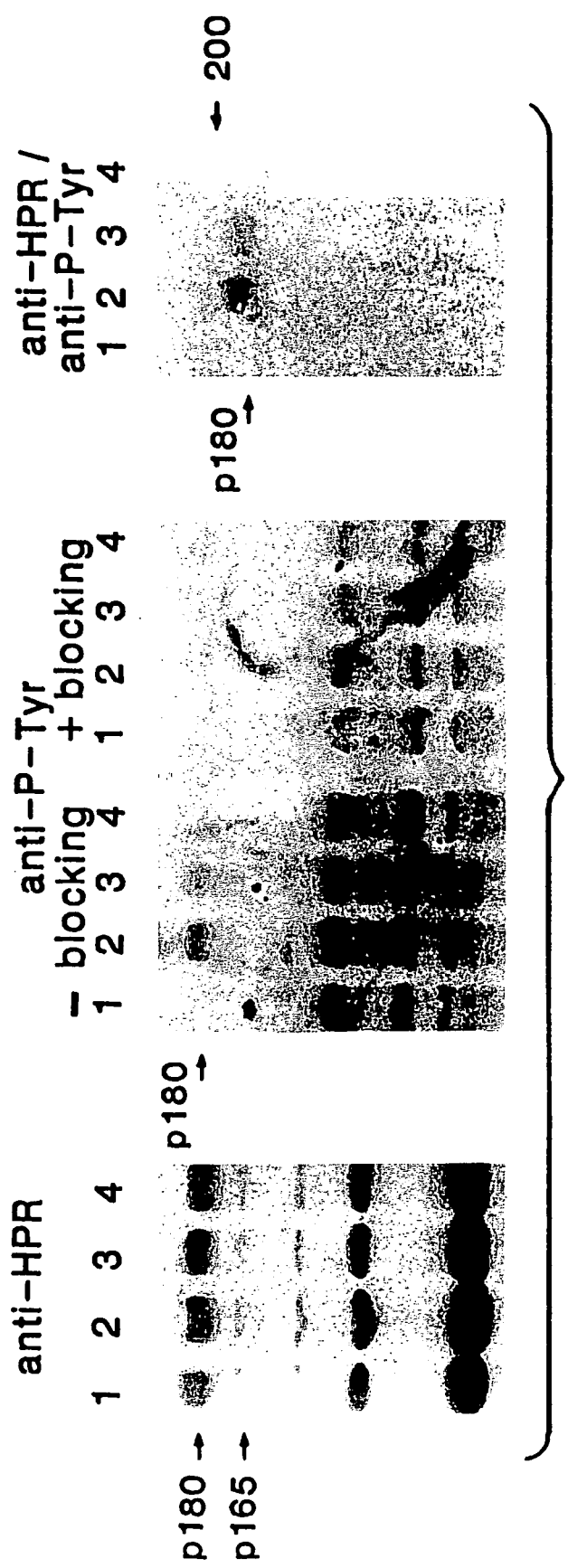

Exposure of 8387 cells, which expressed only the type α PDGF gene product, to the same amount of each respective PDGF isoform revealed a very different pattern of receptor autophosphorylation. Here, PDGF-BB induced the highest level of autophosphorylation of the 180 kd species specifically recognized by anti-type β PDGF-R serum (anti-HPR), and human PDGF induced detectable autophosphorylation as well (FIG. 9B). In contrast, PDGF-AA induced no detectable phosphorylation.

Thus, while PDGF-AB and PDGF-BB triggered both receptors, the much stronger response of the β type receptor to the BB homodimer as well as its lack of detectable response to the AA homodimer readily distinguished the receptors functionally.

To investigate the pattern of autophosphorylation of the two receptors by different PDGF isoforms in the same cells, NIH/3T3 cells were first triggered by different ligands followed by immunoprecipitation with either anti-type α or β PDGF-R serum. The immunoprecipitated receptor proteins were then analyzed by immunoblotting with anti-phosphotyrosine serum.

Figure 9C:
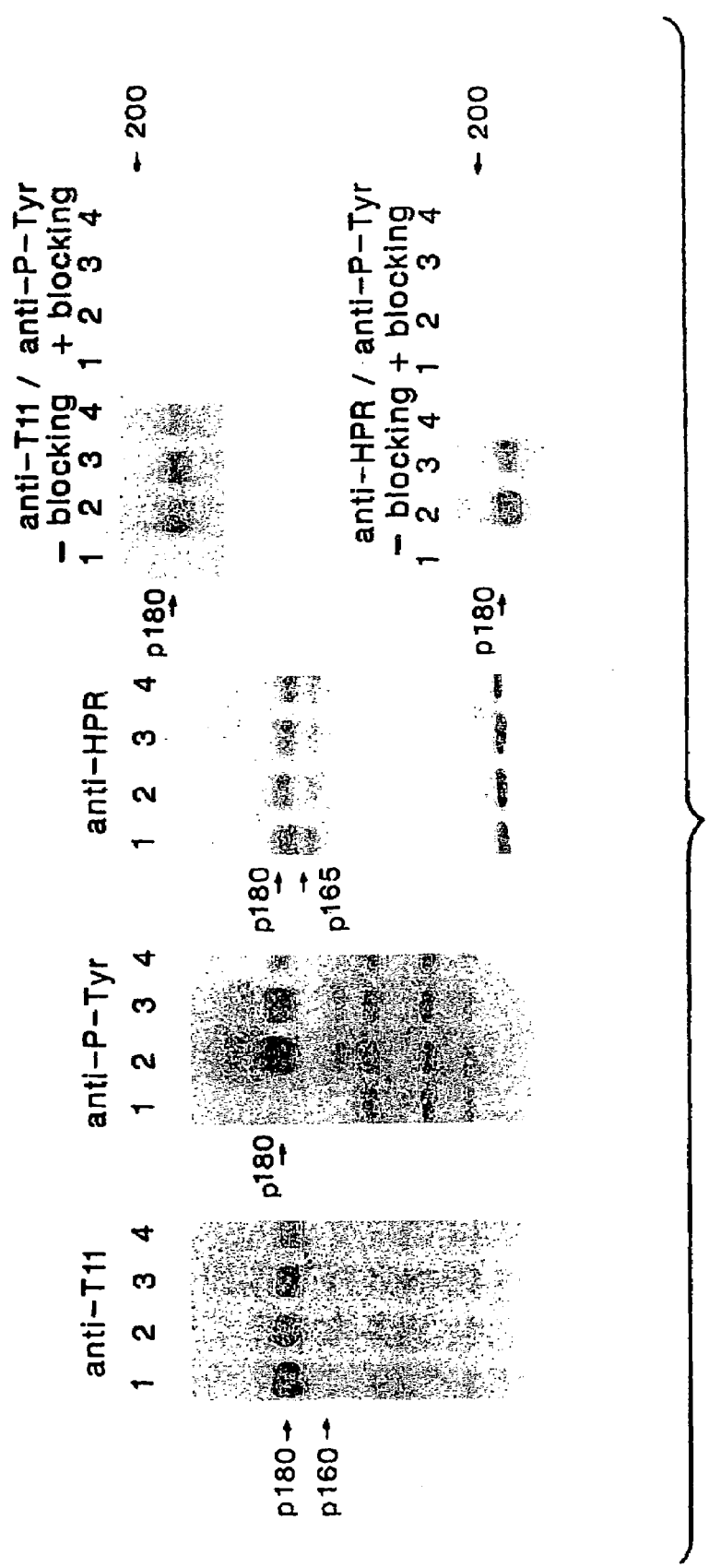

As shown in FIG. 9C, the 180 kd protein immunoprecipitated by the type α PDGF-R antiserum was phosphorylated by all three dimeric forms of PDGF. In contrast, the 180 kd phosphoprotein immunoprecipitated by the anti-type β receptor serum was detected only after human PDGF-AB or PDGF-BB stimulation. Thus, the patterns of response to different PDGF ligands, remained receptor-specific in at one example of nontransformed cells naturally expressing both PDGF-R genes.

Type a PDGF receptor is more-efficient in stimulating DNA synthesis in response to PDGF isoform AB. The expression of the two receptors in other fibroblast lines was analyzed next. Western blotting analysis (data not shown) revealed significant variations in the ratio of the two receptors among the lines analyzed. Whereas mouse fibroblasts expressed similar levels of type α and type β receptors, human fibroblasts such as AG1523 or M413 expressed relatively lower levels of the type α receptor than either mouse fibroblasts or M426 human fibroblasts.

Figure 10B:
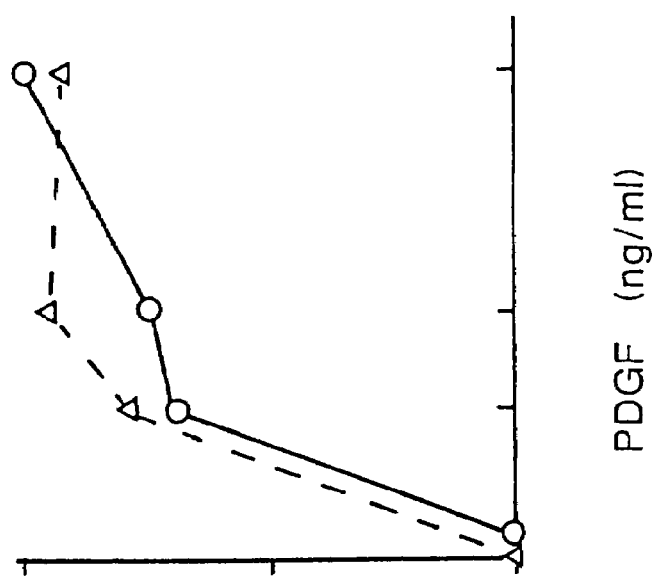
FIG. 10 Stimulation of DNA synthesis by PDGF-AB (triangles) or PDGF-BB (circles) in various cells, as follows: (A) mouse NIH/3T3; (B) human M426; (C) human AG1523; (D) human M413.
Figure 10A:
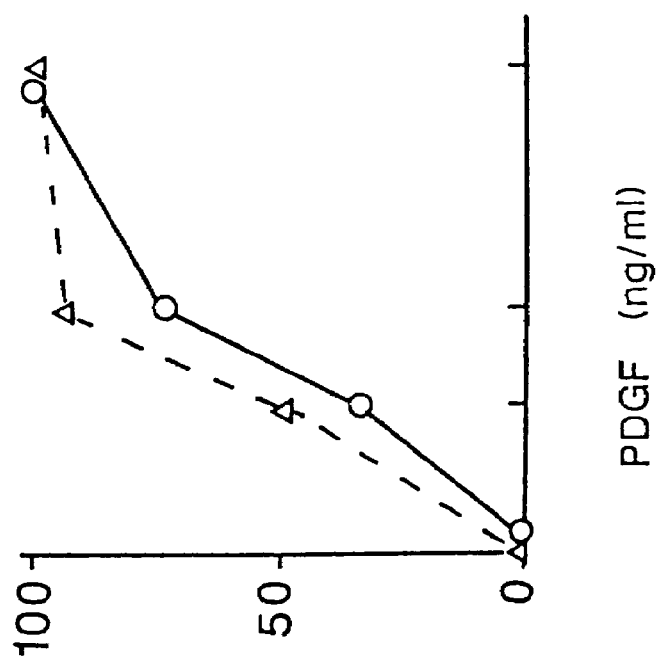

Saturating amounts of PDGF-AB or PDGF-BB yielded similar increases in DNA synthesis in each of the cell lines (data not shown). However, submaximal doses of PDGF-AB and PDGF-BB showed significant differences in the levels of mitogenic activity observed (FIG. 10). Whereas, NIH/3T3, BALB/3T3 and M426 cells responded with comparable efficiency to PDGF-BB and AB, PDGF-AB was significantly less active on AG1523 or M413 cells. Their lesser mitogenic responsiveness to PDGF-AB seemed to correlate with the high ratio of β to α receptors in these cells detected immunologically.

Taken together with the dose-response curves observed for phosphorylation of the two receptors in NIH/3T3 cells by the different PDGF isoforms, these results strongly suggested preferential triggering of the type α receptor, in the presence of the type β receptor, by PDGF-AB, as well as by PDGF-AA.

Independent expression of two PDGF gene types after introduction of cDNAs into PDGF receptor-free hematopoietic cells. To investigate the biological and biochemical responses specific to each PDGF-R gene product, systems were developed to look at this receptor in cells in which each type could be independently introduced and expressed. These systems were based on the 32D cell line, a mouse hematopoietic cell line normally dependent on Il-3 for survival and proliferation. Recent studies have established that introduction of an expression vector for the EGF-R in these cells led to effective coupling with EGF mitogenic signal transduction pathways.

The mammalian expression vectors described above, carrying the gpt selectable marker, was used to transfect 32D cells with either the type α or the type β PDGF-R cDNAs by electroporation. Transformants were selected using medium supplemented with mycophenolic acid. After 2 weeks in the selective medium, viable cultures were obtained.

Cultures designated 32D-αR and 32D-βR, respectively were subjected to Northern blot analysis, as described above. Neither type of PDGF-R mRNA was detectable in the parental 32D cells even under relaxed hybridization conditions, which conditions enabled detection of the respective mouse PDGF-R gene transcripts in NIH/3T3 fibroblasts. In contrast, 32-αR and 32D-βR transfectants expressed abundant transcripts specific to the human type α and type β PDGF-R genes, respectively. When membrane lysates of these transfectant were subjected to immunoblot analysis, anti-type α PDGF-R peptide serum detected 180 kd and 160 kd protein species in 32D-αR but not in 32D-β cells. Moreover, these proteins were specifically competed by the immunizing peptide. Conversely, 32D-βR cells contained 180-200 kd and a 165 kd species which were specifically detected by the anti-type β PDGF-R serum. None of these proteins species were detectable in control 32D cells.

Figure 11:
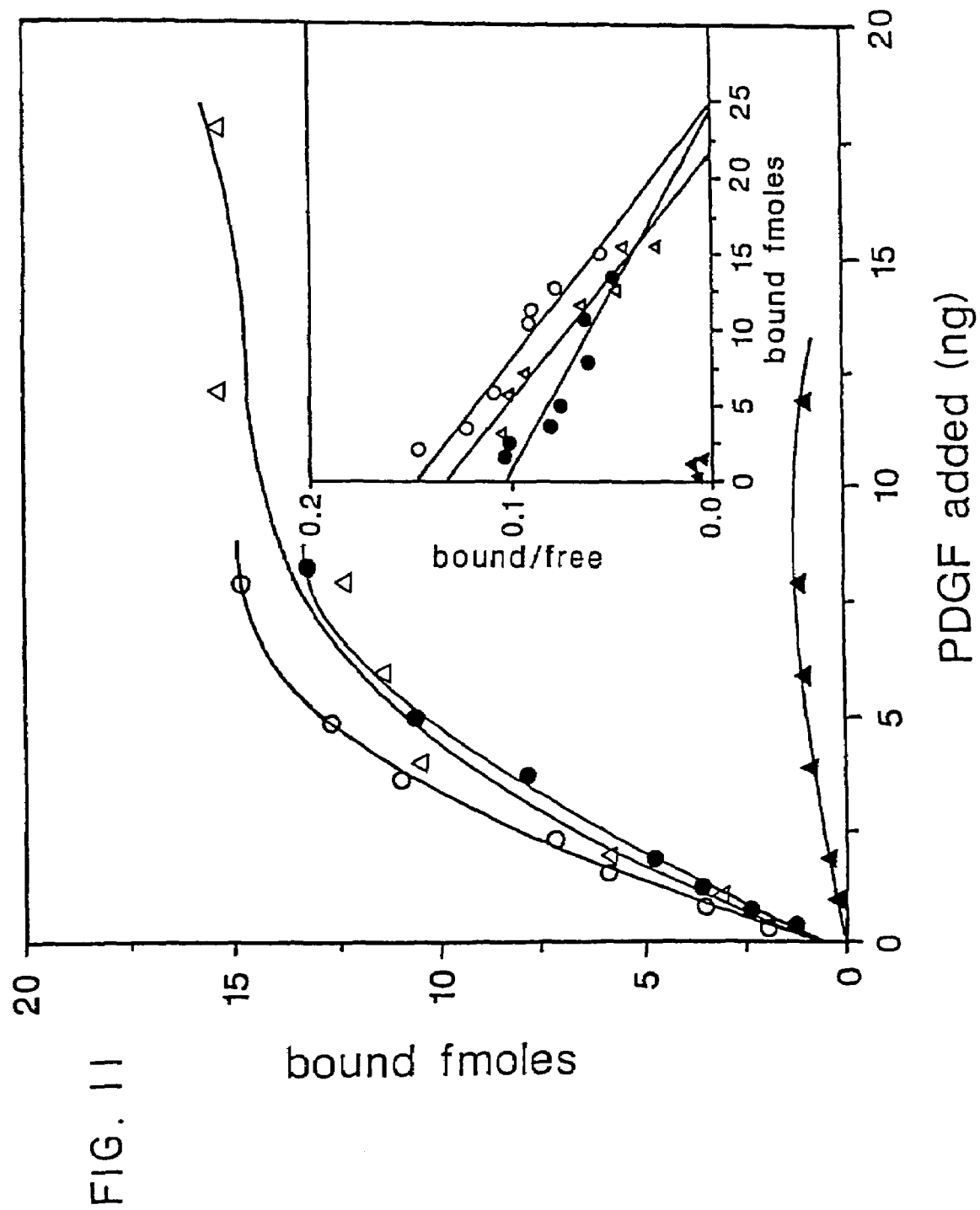
FIG. 11 Receptor binding of PDGF-AB (triangles) or PDGF-BB (circles) by human D32 cells reconstituted with type α (open symbols) or type β (filled symbols) PDGF receptors by transfection with vectors bearing the respective cDNAs. The inset displays the same data replotted in the standard (semi-log) Scatchard format.

Type α receptor has a higher binding affinity for the PDGF-AB isoform. PDGF-BB binding was compared in 32D-αR or 32D-βR transfectants, and both showed high affinity binding. Scatchard analysis revealed about two thousand receptors per cell with a single affinity class of binding sites. The Kds were 0.4 nM and 0.5 nM for 32D-αR and 32D-βR cells, respectively (FIG. 11). 32D-αR cells also showed a high binding affinity ($K_d$=0.4 nM) for $^{125}$I-PDGF-AB, exhibiting the same number of binding sites as for PDGF-BB.

In contrast, however, 32D-βR cells revealed ten times less binding capacity for $^{125}$I-PDGF-AB than did 32D-αR cells. Thus, standardized on the basis of their similar binding of PDGF-BB, the type β receptor showed a strikingly lower affinity for PDGF-AB.

Common biological functions independently triggered by type α and β PDGF gene products. Mitogenesis and chemotaxis are among the most well characterized responses of fibroblasts to PDGF. Thus, whether 32D-αR or βR lines mediated either of these biological responses was investigated.

Figure 12A:
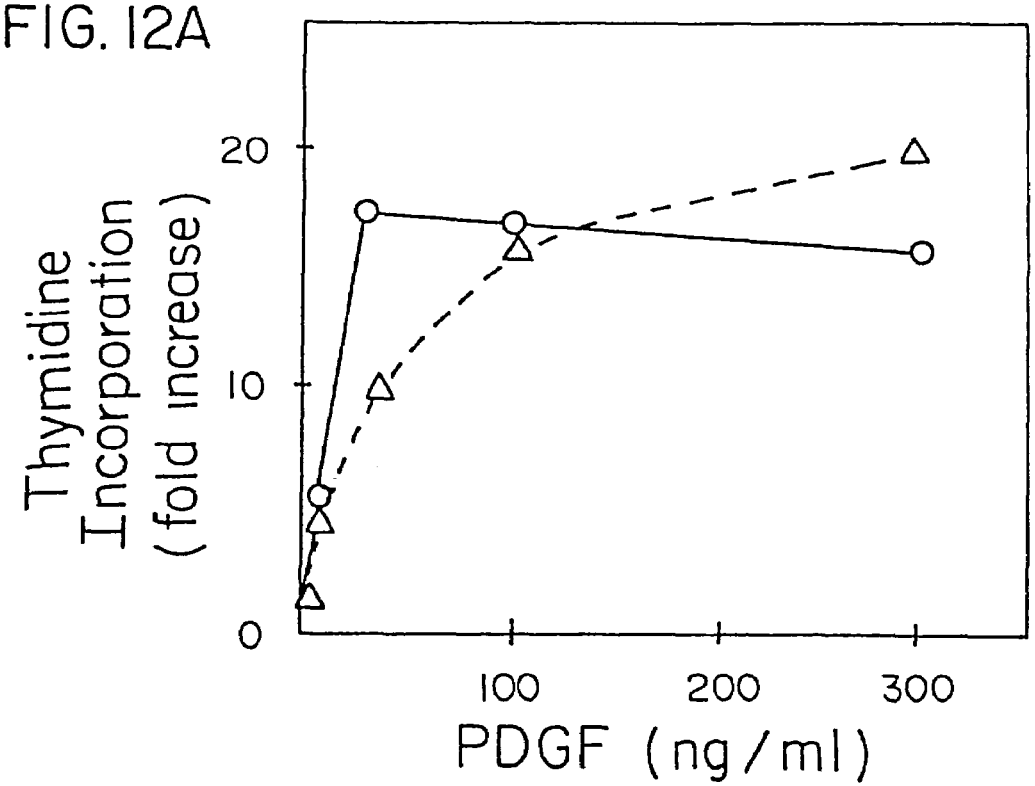
FIG. 12 DNA synthesis stimulation responses to PDGF-AB (triangles) or PDGF-BB (circles) by human D32 cells reconstituted with type α (upper panel) or type β (lower panel) PDGF receptors.
Figure 12B:
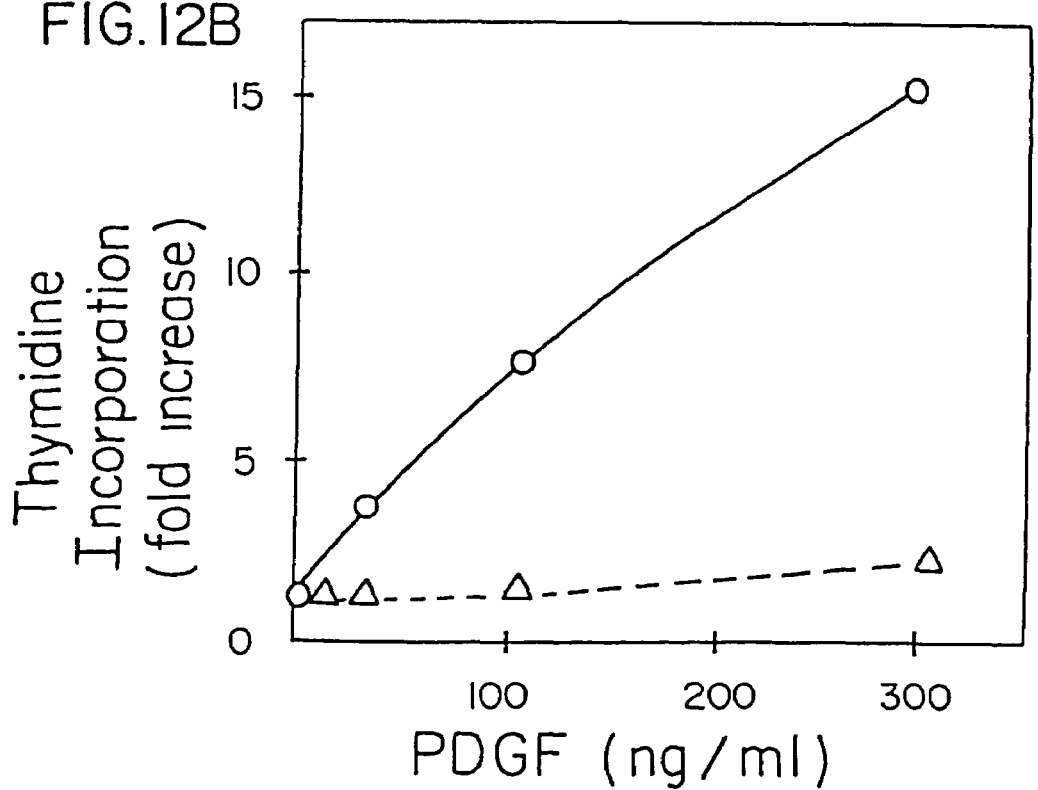

Growth of 32D cells is normally strictly dependent on IL-3, and deprivation of IL-3 from the medium led to the rapid loss of viability both of the transfectants and the control 32D cells. As shown in FIG. 12, PDGF-BB was able to couple efficiently with mitogenic signal transduction pathways and abrogate IL-3 dependence in a similar does dependent manner in both transfectants, but had no effect in control 32D cells. Thus, the presence of either type α or β. PDGF-R was both necessary and sufficient for the mitogenic response to PDGF BB.

However, whereas, the type α receptor containing 32D cells were as responsive to PDGF-AB as to PDGF-BB, PDGF-AB elicited a significantly lesser DNA synthesis response in 32D-βR cells (FIG. 12).

These findings were confirmed by analysis of colony-formation in semi-solid agar containing medium. Both transfectants formed colonies readily in PDGF-BB, supplemented medium but only 32D-∀R cells did so in medium supplemented with PDGF-AB (data not shown). Thus, the mitogenic responses observed with both 32D-αR and βR transfectants correlated well with the binding properties of the same PDGF isoforms to α and β receptors expressed by each cell line, respectively.

Figure 13A:
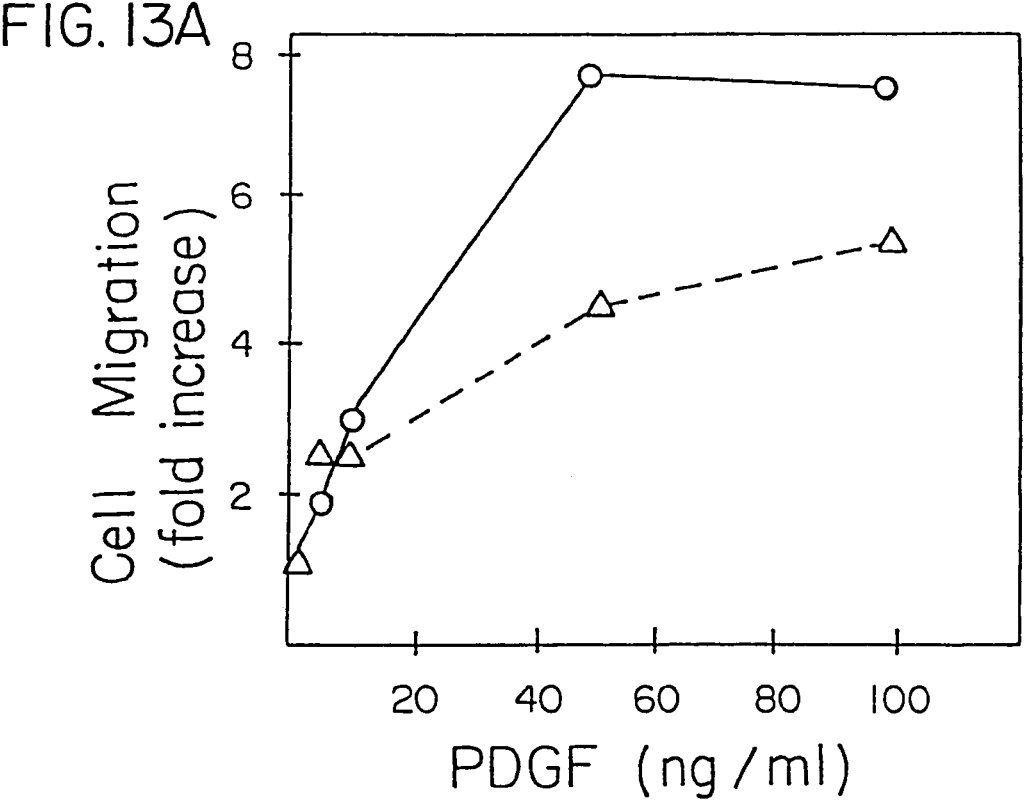
FIG. 13 Chemotaxic responses to PDGF-AB (triangles) or PDGF-BB (circles) by human D32 cells reconstituted with type α (upper panel) or type β (lower panel) PDGF receptors.
Figure 13B:
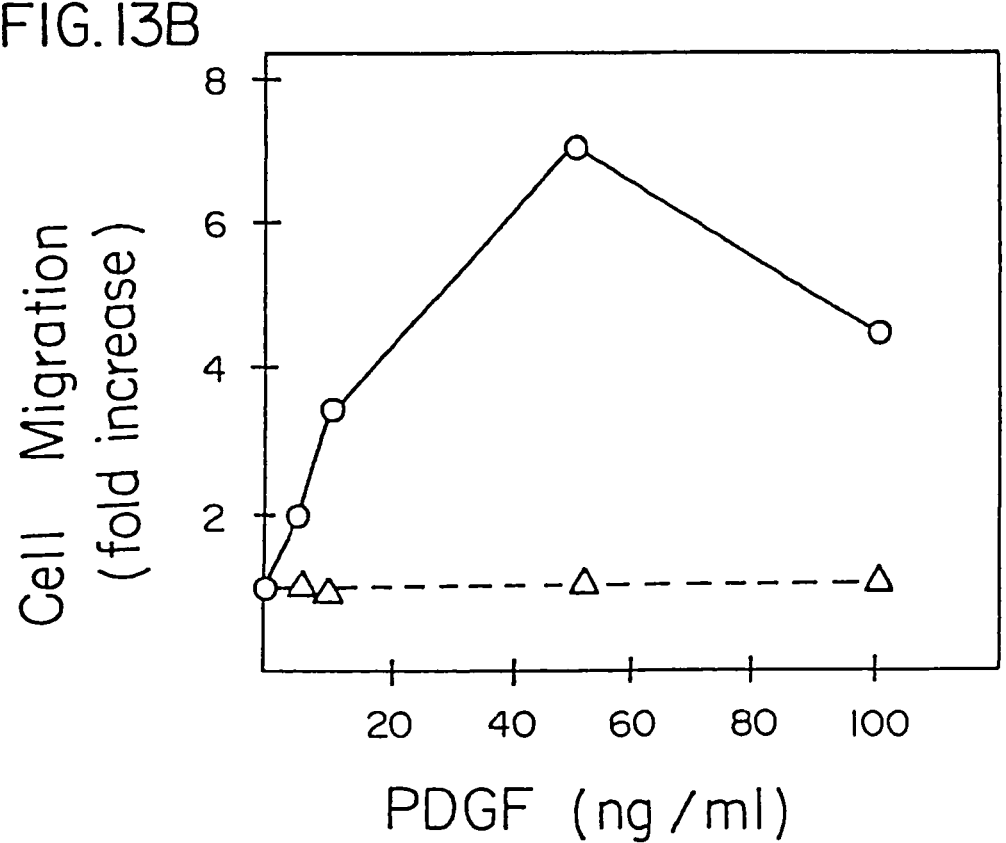

To address whether chemotaxis was specifically mediated by either type α or PDGF receptors, a chemotaxis assay was employed using the modified Boyden chamber technique well known in the art. While 32D cells lacking PDGF receptors did not respond to PDGF-AB or PDGF-BB, PDGF-BB was chemotaxic for both α and β receptor expressing transfectants. PDGF-AB was relatively more active on 32D-αR cells (FIG. 13).

Thus, each PDGF receptor independently coupled with both mitogenic and chemotaxis signalling pathways inherently present in 32D cells. Moreover, these functions were triggered according to the relative binding abilities of PDGF isoforms to either receptor.

Inositol lipid metabolism and cytosolic $Ca^{2+}$ mobilization coupling with independently reconstituted receptors. Recent investigations have suggested an important role of receptor-mediated turnover of inositol lipids resulting in the increase of second messengers such as intracellular free calcium and diacyloglycerol in the transduction of the PDGF-induced mitogenic signal. Thus, the effects of PDGF-AB and PDGF-BB on inositol lipid metabolism and intracellular free $Ca^{2+}$ ($[Ca^{2+}]i$) were studied in type α and type β PDGF-R containing 32D cells.

The accumulation of radioactive inositol phosphates was measured after prelabelling cultures with $^3H$-myoinositol and challenge with PDGF isoforms at 37° C. in the presence of LiCl, according to methods well known in the art. $[Ca^{2+}]i$ was measured in 32D cells in suspension, loaded with the fluorescent $[Ca^{2+}]i$ indicator fura-2, and treated with PDGFs in the complete incubation medium.

FIG. 14 shows the effect of PDGF-AB and PDGF-BB on inositol phosphate formation and $[Ca^{2+}]i$ in type α and type β PDGF-R 32D cells. As shown in FIG. 14 (panel A), both PDGF-BB and PDGF-AB were able to elicit dose-dependent accumulation of inositol phosphates, with similar relative potencies. The same isoforms exerted almost identical increases in $[Ca^{2+}]i$ in type α PDGF-R 32D cells as well (FIG. 14, panel A, insert). PDGF-BB also markedly stimulated inositol lipid metabolism and intracellular $Ca^{2+}$ mobilization in type β PDGF-R 32D cells, establishing the very similar biochemical responses elicited by these distinct PDGF-R gene products in 32D cells in response to PDGF-BB.

FIG. 14 (panel B) shows that PDGF-AB was significantly less effective than PDGF-BB in promoting inositol phosphate accumulation in type β PDGF-R 32D cells. Detectable release of inositol phosphate occurred only at high PDGF-AB concentration. Similarly, PDGF-AB elicited little or no $(Ca^{2+})i$ response.

Discussion

The present studies demonstrate the existence of two distinct human PDGF receptor genes. Further, they illustrate the detection and isolation of two principal embodiments of this invention, the genomic and cDNA clones of a novel gene within the PDGF-R/CSF1-R subfamily. This gene is divergent from but most closely related to the known PDGF-R gene. Under conditions of natural expression as well as following introduction of this novel cDNA into appropriate target cells by means of an expression vector, functional responses of its product to PDGF were demonstrated at concentrations that bound and triggered tyrosine phosphorylation of the previously identified PDGF receptor.

Standardized on the basis of similar levels of tyrosine phosphorylation (and several other activities) of PDGF-R gene product induced by a constant amount of PDGF, the new receptor was shown to respond better than the known PDGF-R to the AA homodimer. Conversely, the known receptor responded preferentially to the BB homodimer. Based upon the present findings, the new gene product has been designated as the type α PDGF-R and the previously identified PDGF-R gene product as the type β receptor.

The AA homodimer failed to stimulate detectable tyrosine phosphorylation of the β type receptor in NIH/3T3 cells and yet is capable of inducing DNA synthesis in this cell line (37). This indicated that the α type receptor can couple with mitogenic signalling pathways in fibroblasts. The β type receptor has also been reported to couple PDGF with mitogenic pathways (28). These results suggested that both receptor gene products can induce a proliferative response.

The ability, according to compositions and methods of this invention, to stably introduce expression vectors for these distinct receptor genes into a null cell made it possible to confirm this suggestion in human cells. Further studies in such cells showed that other known PDGF functions including chemotaxis (38), membrane ruffling (39), as well as transmodulation of a heterologous receptor (40), are not specifically mediated by either type α or β PDGF-R gene products.

Such knowledge is a necessary prelude to understanding and diagnosis of disease conditions affecting these PDGF functions, which can be furthered through additional practice of the present invention.

Among human tumor cell lines analyzed using methods of this invention, several were observed in which there was discoordinate expression of the two PDGF-R genes. Moreover, representative tumor cell lines expressing mRNA from either gene were shown to contain the respective protein product, which bound and was phosphorylated on tyrosine in response to PDGF.

The availability of the immunologic as well as the molecular probes of this invention, specific for either type α or type β PDGF-R gene products, makes it possible to identify human tumors in which expression of the PDGF-A or B chain, in combination with either receptor gene, may be causally implicated in tumor development. At the same time, the availability of reagents for specific detection of each type of component is a critical aid in efforts to implicate the abnormal expression of this complex growth factor-receptor network in other chronic disease states such as arteriosclerosis, arthritis, and fibrotic diseases (23).

Additional observations of scientific import have already been provided by the practice of the invention as herein described. For instance, the chromosomal location of the novel gene, established using DNAs of this invention, provides insight into the possible evolution of this receptor gene family. Thus, the chromosomal localization places the type α PDGF receptor gene on chromosome 4 at 4q 11-12, the same region as c-kit (15), a related receptor-like gene. Other genes of this subfamily have been localized on chromosome 5. These include the type β PDGF-R mapped at 5q 23-31 (6) and the CSFI-R gene, on 5q 33.2-33.3 (29). Thereis evidence for a common ancestral origin of human chromosomes 4 and 5 (30). These related receptor genes cluster near the centromere on 4q or at the distal half of 5q. Thus, if the progenitor(s) of these genes were confined to a single ancestral chromosome, the breakup of linkage might be explained by an inversion within the long arm.

The present studies also establish that different PDGF-R genes encode two receptor types, with binding properties evidently independent of the cell in which each is expressed. The implications of this observation can be better appreciated in light of knowledge about other receptor systems.

There is emerging evidence that as more complex organisms have evolved, mechanisms of intercellular communication have increased in complexity as well. The related EGF and TGF$_\alpha$ molecules interact with similar affinities with a common receptor, the EGF receptor (31). Different patterns of developmental and tissue expression of these growth factors (32) presumably account for their present existence.

There are increasing examples of evolutionarily divergent receptor genes as well. The products of such genes can respond to completely different ligands, as is the case of PDGF and CSF-1 receptors (33, 34), or, alternatively, to related ligands, as with the IGF-I and insulin receptors (35). Here the developmental and tissue specific expression of both the receptors and their ligands, as well as the biochemical responses triggered, have evolved with the complexity of the organism.

As demonstrated in the present studies, the responses mediated by PDGF not only involve different dimeric forms of the related ligands encoded by two genes, but two related genes encoding different PDGF receptors as well. In addition to their differences in tissue specific expression (34, 36), the two PDGF gene products are known to differ in their relative secretory capacity. The PDGF-A chain is much more efficiently released than is the B chain (37), giving the former the possibility of acting at greater distances.

In view of the present evidence of coordinate expression of the two PDGF receptor genes in all normal tissues so far examined, their tissue specific expression may not be a major determinant of their functions. However, application of the methods of the present invention to a comprehensive survey of the expression of each receptor type during embryonic development and in homogeneous normal cell populations may uncover evidence of differential regulation.

REFERENCES

1. R. F. Doolittle et al., Science 221, 275 (1983); M. D. Waterfield et al., Nature 304, 35 (1983); K. C. Robbins et al., ibid. 305, 605 (1983).
2. J. Downward et al., ibid. 307, 521 (1984); A. Ullrich et al., ibid. 309, 418 (1984).
3. C. J. Sherr et al., Cell 41, 665 (1985); L. Coussens et al., Nature 320, 277 (1986).
4. J. M. Bishop, Science 235, 305 (1985); R. A. Weinberg, ibid. 230, 770 (1985); S. K. Hanks, A. M. Quinn, T. Hunter, ibid. 241, 42 (1988).
5. C. R. King, M. H. Kraus, S. A. Aaronson, ibid. 229, 974 (1985); G. D. Kruh et al., ibid. 234, 1545 (1986).
6. Y. Yarden et al., Nature 323, 226 (1986).
7. P. Besmer et al., ibid. 320, 415 (1986); Y. Yarden et al., EMBO J. 6, 3341 (1987).
8. D. Q. Xu, S. Guilhot, F. Galibert, Proc. Natl. Acad. Sci. USA 82, 2862 (1985).
9. R. Breathnad and P. Chambon, Annu. Rev. Biochem. 50, 349 (1981).
10. Subject of the U.S. Patent Application entitled "Efficient Directional Cloning System", to be filed February, 1989.
11. M. Kozak, Cell 44, 283 (1986).
12. G. von Heijne, Nucleic Acids Res. 14, 4683 (1986).
13. J. E. Smart et al., Proc. Natl. Acad. Sci USA 78, 6013 (1981).
14. R. G. K. Gronwald et al., ibid. 88, 3435 (1988); L. Claesson-Welsh et al., Mol. Cell. Biol. 8, 3476 (1988).
15. L. d'Auriol et al., Hum. Genet 78, 374 (1988).
16. C. A. Griffin et al., Cytogenetic Cell Genet 45, 67 (1987).
17. A. D. Luster et al., Proc. Natl. Acad. Sci. USA 84, 2868 (1987).
18. A. Richmond et al., EMBO J. 7, 2025 (1988).
19. M. E. Harper and G. Dugaiczyk, J. Hum. Genet. 35, 565 (1983).
20. M. A. Furguson-Smith et al., Cytogenet Cell Genet 40, 628 (1985).
21. S. P. Ball, P. J. L. Cook, M. Mars, K. E. Buckton, Ann Hum. Genet 46, 35 (1982).
22. A. R. Frackelton, P. M. Tremble Jr., L. T. Williams, J. Biol. Chem. 259, 7909 (1984); T. O. Daniel et al., Proc. Natl. Acad. Sci. USA 82, 2684 (1985).
23. R. Ross, E. W. Raines, D. F. Bowen-Pope, Cell 46, 155 (1986).
24. A. Johnsson, C.-H. Heldin, B. Westermark, A. Wasteson, Biochem. Biophys. Res. Commun. 104, 66 (1982).
25. C.-H. Heldin et al., Nature 319, 511 (1986).
26. P. Stroobant and M. D. Waterfield, EMBO J. 3, 2963 (1984).
27. C. H. Heldin et al., ibid. 7, 1387 (1988); C. E. Hart et al., Science 240, 1529 (1988).
28. J. A. Escobedo et al., ibid. 240, 1532 (1988).
29. M. M. Le Beau et al., ibid. 231, 984 (1986).
30. D. E. Comings, Nature 238, 455 (1972).
31. J. Massague, J. Biol. Chem. 258, 13614 (1983).
32. R. Derynck et al., Cancer Res. 47, 707 (1987); D. C. Lee et al., Mol. Cell. Biol. 5, 3644 (1985); D. R. Twardzik, Cancer Res. 45, 5413 (1985); R. J. Coffey et al., Nature 328, 817 (1987).
33. E. S. Kawasaki et al., Science 230 291 (1985).
34. C. Betsholtz et al., Nature 320, 695 (1986).
35. A. Ullrich et al., Nature 313 (1985); Y. Ebina et al., Cell 40, 747 (1985); A. Ullrich et al., EMBO J. 5, 2503 (1986).
36. R. A. Seifert, S. M. Schwartz, D. F. Bowen-Pope, Nature 34, 669 (1984); M. Jaye et al., Science 228, 882 (1985); J. Nilsson et al., Proc. Natl. Acad. Sci. USA 82, 4418 (1985); T. Collins et al., Nature 316, 748 (1985).
37. P. Beckman et al., Science 241, 1346 (1988).
38. H. Seppa et al., J. Cell Biol. 92, 584 (1982); G. R. Grotendorst et al., J. Cell Physiol. 113, 261 (1982); T. F. Deuel, R. M. Senior, J. S. Huang, G. L. Griffin, J. Clin. Invest. 69, 1046 (1982).
39. K. Mellstrom et al., J. Cell Motility and Muscle Res. 4, 589 (1983).

40. E. Rozengurt, M. Rodriquez-Pnena, K. A. Smith, Proc. Natl. Acad. Sci. USA 80, 7244 (1983); R. J. Davis and M. P. Czech, ibid. 82, 4080 (1985).
41. E. M. Southern, J. Med. Biol. 98, 503 (1975).
42. P. W. J. Rigby, M. Dieckerman, C. Rhodes, P. Berg ibid. 113, 237 (1977).
43. G. M. Wahl, M. Stem, G. R. Stark, Proc. Natl. Acad. Sci. USA 76, 3683 (1979).
44. A. Hampe, M. Gobet, C. J. Sherr, F. Galibert, ibid. 81, 85 (1984).
45. F. Sanger, S. Nicklen, A. R. Coulson, ibid. 74, 5463 (1977).
46. J. Kyte and R. F. Doolittle, J. Mol. Biol. 157, 105 (1982).
47. M. E. Harper and G. F. Saunders, Chromosoma (Berl.) 83, 431 (1981); N. C. Popescu et al., Cytogenet. Cell Genet 39, 73 (1985).
48. H. D. Lehrach, D. Diamond, J. M. Wozney, H. Boedtker, Biochemistry 16, 4743 (1977).
49. C. R. King, N. A. Giese, K. C. Robbins, S. A. Aaronson, Proc. Natl. Acad. Sci. USA 82, 5295 (1985).
50. M. Wigler et al., Cell 11, 223 (1977).
51. H. Towbin, T. Staehelin, J. Gordon, Proc. Natl. Acad. Sci. USA 76, 4350 (1979).
52. W. M. Hunter and F. C. Greenwood, Nature 194, 495 (1962).
53. E. W. Raines and R. Ross, J. Biol. Chem. 257, 5154 (1982).
54. J. J. Wang, Mol. Cell. Biol. 5, 3640 (1985).

For purposes of completing the background description and present disclosure, each of the published articles, patents and patent applications heretofore identified in this specification are hereby incorporated by reference into the specification.

The foregoing invention has been described in some detail for purposes of clarity and understanding. It will also be obvious that various combinations in form and detail can be made without departing from the scope of the invention.

What is claimed is:

1. A method of determining the ability of a compound to bind to Platelet-derived growth factor receptor alpha (α PDGFR) comprising:
   a) providing a sample of cells having a recombinant construct expressing α PDGFR;
   b) exposing said sample of cells expressing α PDGFR to a compound suspected of binding to α PDGFR; and
   c) measuring the amount of α PDGFR activity after exposure of the cell sample.

2. The method of claim 1, wherein the compound is an agonist of α PDGFR activity.

3. The method of claim 1, wherein the compound is an antagonist of α PDGFR activity.

4. The method of claim 1, wherein the ability of the compound to bind to α PDGFR is compared to the ability of the PDGF AA isoform to bind to α PDGFR.

5. The method of claim 1, wherein the ability of the compound to bind to α PDGFR is compared to the ability of the PDGF AB isoform to bind to α PDGFR.

6. The method of claim 1, wherein the ability of the compound to bind to α PDGFR is compared to the binding ability of an antibody or fragment thereof that binds to α PDGFR but not to β PDGFR.

7. The method of claim 1, wherein the cells expressing α PDGFR are a cell line expressing α PDGFR.

* * * * *

SEQUENCE LISTING

```
<160> NUMBER OF SEQ ID NOS: 2

<210> SEQ ID NO 1
<211> LENGTH: 6412
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: CDS
<222> LOCATION: (139)...(3406)

<400> SEQUENCE: 1
ccattactgt tggagctaca gggagagaaa caggaggaga ctgcaagaga tcatttggga        60
aggccgtggg cacgctcttt actccatgtg tgggacattc attgcggaat aacatcggag       120
gagaagtttc ccagagct atg ggg act tcc cat ccg gcg ttc ctg gtc tta        171
                    Met Gly Thr Ser His Pro Ala Phe Leu Val Leu
                     1               5                   10 ggc tgt ctt ctc aca ggg ctg agc cta atc ctc tgc cag ctt tca tta        219
Gly Cys Leu Leu Thr Gly Leu Ser Leu Ile Leu Cys Gln Leu Ser Leu
             15                  20                  25 ccc tct atc ctt cca aat gaa aat gaa aag gtt gtg cag ctg aat tca        267
Pro Ser Ile Leu Pro Asn Glu Asn Glu Lys Val Val Gln Leu Asn Ser
         30                  35                  40 tcc ttt tct ctg aga tgc ttt ggg gag agt gaa gtg agc tgg cag tac        315
Ser Phe Ser Leu Arg Cys Phe Gly Glu Ser Glu Val Ser Trp Gln Tyr
     45                  50                  55 ccc atg tct gaa gaa gag agc tcc gat gtg gaa atc aga aat gaa gaa        363
Pro Met Ser Glu Glu Glu Ser Ser Asp Val Glu Ile Arg Asn Glu Glu
 60                  65                  70                  75 aac aac agc ggc ctt ttt gtg acg gtc ttg gaa gtg agc agt gcc tcg        411
Asn Asn Ser Gly Leu Phe Val Thr Val Leu Glu Val Ser Ser Ala Ser
                 80                  85                  90 gcg gcc cac aca ggg ttg tac act tgc tat tac aac cac act cag aca        459
Ala Ala His Thr Gly Leu Tyr Thr Cys Tyr Tyr Asn His Thr Gln Thr
             95                 100                 105 gaa gag aat gag ctt gaa ggc agg cac att tac atc tat gtg cca gac        507
Glu Glu Asn Glu Leu Glu Gly Arg His Ile Tyr Ile Tyr Val Pro Asp
        110                 115                 120
```

```
                                                    -continued cca gat gta gcc ttt gta cct cta gga atg acg gat tat tta gtc atc      555
Pro Asp Val Ala Phe Val Pro Leu Gly Met Thr Asp Tyr Leu Val Ile
125                 130                 135 gtg gag gat gat gat tct gcc att ata cct tgt cgc aca act gat ccc      603
Val Glu Asp Asp Asp Ser Ala Ile Ile Pro Cys Arg Thr Thr Asp Pro
140                 145                 150                 155 gag act cct gta acc tta cac aac agt gag ggg gtg gta cct gcc tcc      651
Glu Thr Pro Val Thr Leu His Asn Ser Glu Gly Val Val Pro Ala Ser
                160                 165                 170 tac gac agc aga cag ggc ttt aat ggg acc ttc act gta ggg ccc tat      699
Tyr Asp Ser Arg Gln Gly Phe Asn Gly Thr Phe Thr Val Gly Pro Tyr
                175                 180                 185 atc tgt gag gcc acc gtc aaa gga aag aag ttc cag acc atc cca ttt      747
Ile Cys Glu Ala Thr Val Lys Gly Lys Lys Phe Gln Thr Ile Pro Phe
            190                 195                 200 aat gtt tat gct tta aaa gca aca tca gag ctg gat cta gaa atg gaa      795
Asn Val Tyr Ala Leu Lys Ala Thr Ser Glu Leu Asp Leu Glu Met Glu
205                 210                 215 gct ctt aaa acc gtg tat aag tca ggg gaa acg att gtg gtc acc tgt      843
Ala Leu Lys Thr Val Tyr Lys Ser Gly Glu Thr Ile Val Val Thr Cys
220                 225                 230                 235 gct gtt ttt aac aat gag gtg gtt gac ctt caa tgg act tac cct gga      891
Ala Val Phe Asn Asn Glu Val Val Asp Leu Gln Trp Thr Tyr Pro Gly
                240                 245                 250 gaa gtg aaa ggc aaa ggc atc aca atg ctg gaa gaa atc aaa gtc cca      939
Glu Val Lys Gly Lys Gly Ile Thr Met Leu Glu Glu Ile Lys Val Pro
                255                 260                 265 tcc atc aaa ttg gtg tac act ttg acg gtc ccc gag gcc acg gtg aaa      987
Ser Ile Lys Leu Val Tyr Thr Leu Thr Val Pro Glu Ala Thr Val Lys
            270                 275                 280 gac agt gga gat tac gaa tgt gct gcc cgc cag gct acc agg gag gtc     1035
Asp Ser Gly Asp Tyr Glu Cys Ala Ala Arg Gln Ala Thr Arg Glu Val
285                 290                 295 aaa gaa atg aag aaa gtc act att tct gtc cat gag aaa ggt ttc att     1083
Lys Glu Met Lys Lys Val Thr Ile Ser Val His Glu Lys Gly Phe Ile
300                 305                 310                 315 gaa atc aaa ccc acc ttc agc cag ttg gaa gct gtc aac ctg cat gaa     1131
Glu Ile Lys Pro Thr Phe Ser Gln Leu Glu Ala Val Asn Leu His Glu
                320                 325                 330 gtc aaa cat ttt gtt gta gag gtg cgg gcc tac cca cct ccc agg ata     1179
Val Lys His Phe Val Val Glu Val Arg Ala Tyr Pro Pro Pro Arg Ile
                335                 340                 345 tcc tgg ctg aaa aac aat ctg act ctg att gaa aat ctc act gag atc     1227
Ser Trp Leu Lys Asn Asn Leu Thr Leu Ile Glu Asn Leu Thr Glu Ile
            350                 355                 360 acc act gat gtg gaa aag att cag gaa ata agg tat cga agc aaa tta     1275
Thr Thr Asp Val Glu Lys Ile Gln Glu Ile Arg Tyr Arg Ser Lys Leu
365                 370                 375 aag ctg atc cgt gct aag gaa gaa gac agt ggc cat tat act att gta     1323
Lys Leu Ile Arg Ala Lys Glu Glu Asp Ser Gly His Tyr Thr Ile Val
380                 385                 390                 395 gct caa aat gaa gat gct gtg aag agc tat act ttt gaa ctg tta act     1371
Ala Gln Asn Glu Asp Ala Val Lys Ser Tyr Thr Phe Glu Leu Leu Thr
                400                 405                 410 caa gtt cct tca tcc att ctg gac ttg gtc gat gat cac cat ggc tca     1419
Gln Val Pro Ser Ser Ile Leu Asp Leu Val Asp Asp His His Gly Ser
                415                 420                 425 act ggg gga cag acg gtg agg tgc aca gct gaa ggc acg ccg ctt cct     1467
Thr Gly Gly Gln Thr Val Arg Cys Thr Ala Glu Gly Thr Pro Leu Pro
                430                 435                 440
```

```
gat att gag tgg atg ata tgc aaa gat att aag aaa tgt aat aat gaa      1515
Asp Ile Glu Trp Met Ile Cys Lys Asp Ile Lys Lys Cys Asn Asn Glu
            445                 450                 455 act tcc tgg act att ttg gcc aac aat gtc tca aac atc atc acg gag      1563
Thr Ser Trp Thr Ile Leu Ala Asn Asn Val Ser Asn Ile Ile Thr Glu
460                 465                 470                 475 atc cac tcc cga gac agg agt acc gtg gag ggc cgt gtg act ttc gcc      1611
Ile His Ser Arg Asp Arg Ser Thr Val Glu Gly Arg Val Thr Phe Ala
                480                 485                 490 aaa gtg gag gag acc atc gcc gtg cga tgc ctg gct aag aat ctc ctt      1659
Lys Val Glu Glu Thr Ile Ala Val Arg Cys Leu Ala Lys Asn Leu Leu
            495                 500                 505 gga gct gag aac cga gag ctg aag ctg gtg gct ccc acc ctg cgt tct      1707
Gly Ala Glu Asn Arg Glu Leu Lys Leu Val Ala Pro Thr Leu Arg Ser
        510                 515                 520 gaa ctc acg gtg gct gct gca gtc ctg gtg ctg ttg gtg att gtg atc      1755
Glu Leu Thr Val Ala Ala Ala Val Leu Val Leu Leu Val Ile Val Ile
525                 530                 535 atc tca ctt att gtc ctg gtt gtc att tgg aaa cag aaa ccg agg tat      1803
Ile Ser Leu Ile Val Leu Val Val Ile Trp Lys Gln Lys Pro Arg Tyr
540                 545                 550                 555 gaa att cgc tgg agg gtc att gaa tca atc agc ccg gat gga cat gaa      1851
Glu Ile Arg Trp Arg Val Ile Glu Ser Ile Ser Pro Asp Gly His Glu
                560                 565                 570 tat att tat gtg gac ccg atg cag ctg cct tat gac tca aga tgg gag      1899
Tyr Ile Tyr Val Asp Pro Met Gln Leu Pro Tyr Asp Ser Arg Trp Glu
            575                 580                 585 ttt cca aga gat gga cta gtg ctt ggt cgg gtc ttg ggg tct gga gcg      1947
Phe Pro Arg Asp Gly Leu Val Leu Gly Arg Val Leu Gly Ser Gly Ala
        590                 595                 600 ttt ggg aag gtg gtt gaa gga aca gcc tat gga tta agc cgg tcc caa      1995
Phe Gly Lys Val Val Glu Gly Thr Ala Tyr Gly Leu Ser Arg Ser Gln
605                 610                 615 cct gtc atg aaa gtt gca gtg aag atg cta aaa ccc acg gcc aga tcc      2043
Pro Val Met Lys Val Ala Val Lys Met Leu Lys Pro Thr Ala Arg Ser
620                 625                 630                 635 agt gaa aaa caa gct ctc atg tct gaa ctg aag ata atg act cac ctg      2091
Ser Glu Lys Gln Ala Leu Met Ser Glu Leu Lys Ile Met Thr His Leu
                640                 645                 650 ggg cca cat ttg aac att gta aac ttg ctg gga gcc tgc acc aag tca      2139
Gly Pro His Leu Asn Ile Val Asn Leu Leu Gly Ala Cys Thr Lys Ser
            655                 660                 665 ggc ccc att tac atc atc aca gag tat tgc ttc tat gga gat ttg gtc      2187
Gly Pro Ile Tyr Ile Ile Thr Glu Tyr Cys Phe Tyr Gly Asp Leu Val
        670                 675                 680 aac tat ttg cat aag aat agg gat agc ttc ctg agc cac cac cca gag      2235
Asn Tyr Leu His Lys Asn Arg Asp Ser Phe Leu Ser His His Pro Glu
685                 690                 695 aag cca aag aaa gag ctg gat atc ttt gga ttg aac cct gct gat gaa      2283
Lys Pro Lys Lys Glu Leu Asp Ile Phe Gly Leu Asn Pro Ala Asp Glu
700                 705                 710                 715 agc aca cgg agc tat gtt att tta tct ttt gaa aac aat ggt gac tac      2331
Ser Thr Arg Ser Tyr Val Ile Leu Ser Phe Glu Asn Asn Gly Asp Tyr
                720                 725                 730 atg gac atg aag cag gct gat act aca cag tat gtc ccc atg cta gaa      2379
Met Asp Met Lys Gln Ala Asp Thr Thr Gln Tyr Val Pro Met Leu Glu
            735                 740                 745 agg aaa gag gtt tct aaa tat tcc gac atc cag aga tca ctc tat gat      2427
Arg Lys Glu Val Ser Lys Tyr Ser Asp Ile Gln Arg Ser Leu Tyr Asp
```

-continued

|     |     |     |     | 750 |     |     |     |     | 755 |     |     |     |     | 760 |     |     |      |
| --- | --- | --- | --- | --- | --- | --- | --- | --- | --- | --- | --- | --- | --- | --- | --- | --- | ---- |
| cgt | cca | gcc | tca | tat | aag | aag | aaa | tct | atg | tta | gac | tca | gaa | gtc | aaa |     | 2475 |
| Arg | Pro | Ala | Ser | Tyr | Lys | Lys | Lys | Ser | Met | Leu | Asp | Ser | Glu | Val | Lys |     |      |
|     | 765 |     |     |     |     | 770 |     |     |     |     | 775 |     |     |     |     |     |      |

```
aac ctc ctt tca gat gat aac tca gaa ggc ctt act tta ttg gat ttg      2523
Asn Leu Leu Ser Asp Asp Asn Ser Glu Gly Leu Thr Leu Leu Asp Leu
780             785                 790                 795 ttg agc ttc acc tat caa gtt gcc cga gga atg gag ttt ttg gct tca      2571
Leu Ser Phe Thr Tyr Gln Val Ala Arg Gly Met Glu Phe Leu Ala Ser
                800                 805                 810 aaa aat tgt gtc cac cgt gat ctg gct gct cgc aac gtc ctc ctg gca      2619
Lys Asn Cys Val His Arg Asp Leu Ala Ala Arg Asn Val Leu Leu Ala
            815                 820                 825 caa gga aaa att gtg aag atc tgt gac ttt ggc ctg gcc aga gac atc      2667
Gln Gly Lys Ile Val Lys Ile Cys Asp Phe Gly Leu Ala Arg Asp Ile
        830                 835                 840 atg cat gat tcg aac tat gtg tcg aaa ggc agt acc ttt ctg ccc gtg      2715
Met His Asp Ser Asn Tyr Val Ser Lys Gly Ser Thr Phe Leu Pro Val
845                 850                 855 aag tgg atg gct cct gag agc atc ttt gac aac ctc tac acc aca ctg      2763
Lys Trp Met Ala Pro Glu Ser Ile Phe Asp Asn Leu Tyr Thr Thr Leu
860                 865                 870                 875 agt gat gtc tgg tct tat ggc att ctg ctc tgg gag atc ttt tcc ctt      2811
Ser Asp Val Trp Ser Tyr Gly Ile Leu Leu Trp Glu Ile Phe Ser Leu
                880                 885                 890 ggt ggc acc cct tac ccc ggc atg atg gtg gat tct act ttc tac aat      2859
Gly Gly Thr Pro Tyr Pro Gly Met Met Val Asp Ser Thr Phe Tyr Asn
            895                 900                 905 aag atc aag agt ggg tac cgg atg gcc aag cct gac cac gct acc agt      2907
Lys Ile Lys Ser Gly Tyr Arg Met Ala Lys Pro Asp His Ala Thr Ser
        910                 915                 920 gaa gtc tac gag atc atg gtg aaa tgc tgg aac agt gag ccg gag aag      2955
Glu Val Tyr Glu Ile Met Val Lys Cys Trp Asn Ser Glu Pro Glu Lys
925                 930                 935 aga ccc tcc ttt tac cac ctg agt gag att gtg gag aat ctg ctg cct      3003
Arg Pro Ser Phe Tyr His Leu Ser Glu Ile Val Glu Asn Leu Leu Pro
940                 945                 950                 955 gga caa tat aaa aag agt tat gaa aaa att cac ctg gac ttc ctg aag      3051
Gly Gln Tyr Lys Lys Ser Tyr Glu Lys Ile His Leu Asp Phe Leu Lys
                960                 965                 970 agt gac cat cct gct gtg gca cgc atg cgt gtg gac tca gac aat gca      3099
Ser Asp His Pro Ala Val Ala Arg Met Arg Val Asp Ser Asp Asn Ala
            975                 980                 985 tac att ggt gtc acc tac aaa aac gag gaa gac aag ctg aag gac tgg      3147
Tyr Ile Gly Val Thr Tyr Lys Asn Glu Glu Asp Lys Leu Lys Asp Trp
        990                 995                 1000 gag ggt ggt ctg gat gag cag aga ctg agc gct gac agt ggc tac atc      3195
Glu Gly Gly Leu Asp Glu Gln Arg Leu Ser Ala Asp Ser Gly Tyr Ile
1005                1010                1015 att cct ctg cct gac att gac cct gtc cct gag gag gag gac ctg ggc      3243
Ile Pro Leu Pro Asp Ile Asp Pro Val Pro Glu Glu Glu Asp Leu Gly
1020                1025                1030                1035 aag agg aac aga cac agc tcg cag acc tct gaa gag agt gcc att gag      3291
Lys Arg Asn Arg His Ser Ser Gln Thr Ser Glu Glu Ser Ala Ile Glu
                1040                1045                1050 acg ggt tcc agc agt tcc acc ttc atc aag aga gag gac gag acc att      3339
Thr Gly Ser Ser Ser Ser Thr Phe Ile Lys Arg Glu Asp Glu Thr Ile
            1055                1060                1065 gaa gac atc gac atg atg gac gac atc ggc ata gac tct tca gac ctg      3387
```

| | |
|---|---|
| Glu Asp Ile Asp Met Met Asp Asp Ile Gly Ile Asp Ser Ser Asp Leu<br>    1070                    1075                   1080 | |
| gtg gaa gac agc ttc ctg t aactggcgga ttcgagggt tccttccact<br>Val Glu Asp Ser Phe Leu<br>    1085 | 3436 |
| tctgggcca cctctggatc ccgttcagaa aaccacttta ttgcaatgcg gaggttgaga | 3496 |
| ggaggacttg gttgatgttt aagagaagt tcccagccaa gggcctcggg gagcgttcta | 3556 |
| aatatgaatg aatgggatat tttgaaatga actttgtcag tgttgcctct cgcaatgcct | 3616 |
| cagtagcatc tcagtggtgt gtgaagtttg gagatagatg gataagggaa taataggcca | 3676 |
| cagaaggtga actttgtgct tcaaggacat tggtgagagt ccaacagaca caatttatac | 3736 |
| tgcgacagaa cttcagcatt gtaattatgt aaataactct aaccaaggct gtgtttagat | 3796 |
| tgtattaact atcttctttg gacttctgaa gagaccactc aatccatcca tgtacttccc | 3856 |
| tcttgaaacc tgatgtcagc tgctgttgaa cttttttaaag aagtgcatga aaaaccattt | 3916 |
| ttgaacctta aaggtactg gtactatagc attttgctat cttttttagt gttaagagat | 3976 |
| aaagaataat aattaaccaa ccttgtttaa tagatttggg tcatttagaa gcctgacaac | 4036 |
| tcatttcat attgtaatct atgtttataa tactactact gttatcagta atgctaaatg | 4096 |
| tgtaataatg taacatgatt tccctccaga gaaagcacaa tttaaaacaa tccttactaa | 4156 |
| gtaggtgatg agtttgacag tttttgacat ttatattaaa taacatgttt ctctataaag | 4216 |
| tatggtaata gctttagtga attaaattta gttgagcata gagaacaaag taaaagtagt | 4276 |
| gttgtccagg aagtcagaat ttttaactgt actgaatagg ttccccaatc catcgtatta | 4336 |
| aaaaacaatt aactgccctc tgaaataatg ggattagaaa caaacaaaac tcttaagtcc | 4396 |
| taaaagttct caatgtagag gcataaacct gtgctgaaca taacttctca tgtatattac | 4456 |
| ccaatggaaa atataatgat cagcaaaaag actggatttg cagaagtttt ttttttttt | 4516 |
| cttcatgcct gatgaaagct ttggcaaccc caatatatgt attttttgaa tctatgaacc | 4576 |
| tgaaagggt cagaaggatg cccagacatc agcctccttc tttcaccct taccccaaag | 4636 |
| agaaagagtt tgaaactcga gaccataaag atattcttta gtggaggctg gatgtgcatt | 4696 |
| agcctggatc ctcagttctc aaatgtgtgt ggcagccagg atgactagat cctgggtttc | 4756 |
| catccttgag attctgaagt atgaagtctg agggaaacca gagtctgtat ttttctaaac | 4816 |
| tccctggctg ttctgatcgg ccagttttcg gaaacactga cttaggtttc aggaagttgc | 4876 |
| catgggaaac aaataatttg aactttggaa cagggttgga attcaaccac gcaggaagcc | 4936 |
| tactatttaa atccttggct tcaggttagt gacatttaat gccatctagc tagcaattgc | 4996 |
| gaccttaatt taactttcca gtcttagctg aggctgagaa agctaaagtt tggttttgac | 5056 |
| aggttttcca aaagtaaaga tgctacttcc cactgtatgg gggagattga actttccccg | 5116 |
| tctcccgtct tctgcctccc actccatacc ccgccaagga aaggcatgta caaaaattat | 5176 |
| gcaattcagt gttccaagtc tctgtgtaac cagctcagtg ttttggtgga aaaacattt | 5236 |
| taagttttac tgataatttg aggttagatg ggaggatgaa ttgtcacatc tatccacact | 5296 |
| gtcaaacagg ttggtgtggg ttcattggca ttctttgcaa tactgcttaa ttgctgatac | 5356 |
| catatgaatg aaacatgggc tgtgattact gcaatcactg tgctatcggc agatgatgct | 5416 |
| ttggaagatg cagaagcaat aataaagtac ttgactacct actggtgtaa tctcaatgca | 5476 |
| agccccaact ttcttatcca acttttcat agtaagtgcg aagactgagc cagattggcc | 5536 |
| aattaaaaac gaaaacctga ctaggttctg tagagccaat tagacttgaa atacgtttgt | 5596 |

```
gtttctagaa tcacagctca agcattctgt ttatcgctca ctctcccttg tacagcctta    5656
ttttgttggt gctttgcatt ttgatattgc tgtgagcctt gcatgacatc atgaggccgg    5716
atgaaacttc tcagtccagc agtttccagt cctaacaaat gctcccacct gaatttgtat    5776
atgactgcat ttgtgggtgt gtgtgtgttt tcagcaaatt ccagatttgt ttccttttgg    5836
cctcctgcaa agtctccaga agaaaatttg ccaatctttc ctactttcta tttttatgat    5896
gacaatcaaa gccggcctga gaaacactat ttgtgacttt taaacgatt agtgatgtcc      5956 ttaaaatgtg gtctgccaat ctgtacaaaa tggtcctatt tttgtgaaga gggacataag    6016
ataaaatgat gttatacatc aatatgtata tatgtatttc tatatagact tggagaatac    6076
tgccaaaaca tttatgacaa gctgtatcac tgccttcgtt tatatttttt taactgtgat    6136
aatccccaca ggcacattaa ctgttgcact tttgaatgtc caaaatttat attttagaaa    6196
taataaaaag aaagatactt acatgttccc aaaacaatgg tgtggtgaat gtgtgagaaa    6256
aactaacttg atagggtcta ccaatacaaa atgtattacg aatgcccctg ttcatgtttt    6316
tgttttaaaa cgtgtaaatg aagatcttta tatttcaata aatgatatat aatttaaagt    6376
taaaaaaaaa aaaaaaaaaa aaaaaaaaaa aaaaaa                              6412
```

<210> SEQ ID NO 2
<211> LENGTH: 1089
<212> TYPE: PRT
<213> ORGANISM: Artificial Sequence
<220> FEATURE:
<223> OTHER INFORMATION: Description of Artificial Sequence; Note = synthetic construct

<400> SEQUENCE: 2

```
Met Gly Thr Ser His Pro Ala Phe Leu Val Leu Gly Cys Leu Leu Thr
 1               5                  10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
```

```
                210                 215                 220
Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
                260                 265                 270

Tyr Thr Leu Thr Val Pro Glu Ala Thr Val Lys Asp Ser Gly Asp Tyr
                275                 280                 285

Glu Cys Ala Ala Arg Gln Ala Thr Arg Glu Val Lys Glu Met Lys Lys
                290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
                340                 345                 350

Asn Leu Thr Leu Ile Glu Asn Leu Thr Glu Ile Thr Thr Asp Val Glu
                355                 360                 365

Lys Ile Gln Glu Ile Arg Tyr Arg Ser Lys Leu Lys Leu Ile Arg Ala
                370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
                420                 425                 430

Val Arg Cys Thr Ala Glu Gly Thr Pro Leu Pro Asp Ile Glu Trp Met
                435                 440                 445

Ile Cys Lys Asp Ile Lys Lys Cys Asn Asn Glu Thr Ser Trp Thr Ile
                450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
                500                 505                 510

Glu Leu Lys Leu Val Ala Pro Thr Leu Arg Ser Glu Leu Thr Val Ala
                515                 520                 525

Ala Ala Val Leu Val Leu Leu Val Ile Val Ile Ile Ser Leu Ile Val
                530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
                595                 600                 605

Glu Gly Thr Ala Tyr Gly Leu Ser Arg Ser Gln Pro Val Met Lys Val
                610                 615                 620

Ala Val Lys Met Leu Lys Pro Thr Ala Arg Ser Ser Glu Lys Gln Ala
625                 630                 635                 640
```

```
                                    -continued

Leu Met Ser Glu Leu Lys Ile Met Thr His Leu Gly Pro His Leu Asn
                    645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
            675                 680                 685

Asn Arg Asp Ser Phe Leu Ser His His Pro Glu Lys Pro Lys Lys Glu
        690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro Asp
    1010                1015                1020

Ile Asp Pro Val Pro Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
                1045                1050                1055
```

```
                                    -continued
Ser Thr Phe Ile Lys Arg Glu Asp Glu Thr Ile Glu Asp Ile Asp Met
            1060                1065                1070

Met Asp Asp Ile Gly Ile Asp Ser Ser Asp Leu Val Glu Asp Ser Phe
        1075                1080                1085

Leu
```